(12) United States Patent
Henriksen

(10) Patent No.: US 11,041,158 B2
(45) Date of Patent: Jun. 22, 2021

(54) OPTIMIZATION METHODS FOR MAKING A SYNTHETIC GENE

(71) Applicant: AgBiome, inc., Research Triangle Park, NC (US)

(72) Inventor: James R. Henriksen, Cary, NC (US)

(73) Assignee: AgBiome, Inc., Durham, NC (US)

( * ) Notice: Subject to any disclaimer, the term of this patent is extended or adjusted under 35 U.S.C. 154(b) by 936 days.

(21) Appl. No.: 15/535,760

(22) PCT Filed: Dec. 21, 2015

(86) PCT No.: PCT/US2015/067024
§ 371 (c)(1),
(2) Date: Jun. 14, 2017

(87) PCT Pub. No.: WO2016/106184
PCT Pub. Date: Jun. 30, 2016

(65) Prior Publication Data
US 2017/0369890 A1 Dec. 28, 2017

Related U.S. Application Data

(60) Provisional application No. 62/095,367, filed on Dec. 22, 2014.

(51) Int. Cl.
| | | |
|---|---|---|
| C12N 15/67 | (2006.01) |
| G16B 25/00 | (2019.01) |
| G16B 30/00 | (2019.01) |
| C12N 15/82 | (2006.01) |
| C07K 14/325 | (2006.01) |

(52) U.S. Cl.
CPC .......... *C12N 15/67* (2013.01); *C07K 14/325* (2013.01); *C12N 15/8216* (2013.01); *G16B 25/00* (2019.02); *G16B 30/00* (2019.02)

(58) Field of Classification Search
None
See application file for complete search history.

(56) References Cited

U.S. PATENT DOCUMENTS

| | | |
|---|---|---|
| 7,741,118 B1 | 6/2010 | Fischhoff et al. |
| 8,175,813 B2 | 5/2012 | Tomso |
| 9,427,003 B2 | 8/2016 | Larrinua et al. |
| 10,774,336 B2 | 9/2020 | Woosley et al. |

FOREIGN PATENT DOCUMENTS

WO 2009049045 4/2009

OTHER PUBLICATIONS

Angov, "Codon usage: Nature's roadmap to expression and folding of proteins.", Biotechnology Journal, vol. 6, No. 6, May 12, 2011, pp. 650-659.
Angov et al., "Heterologous protein expression is enhanced by harmonizing the codon usage frequencies of the target gene with those of the expression host.", PLoS One, vol. 3, No. 5, May 14, 2008, 10 pages.
Gould et al., "Computational tools and algorithms for designing customized synthetic genes.", Front Bioeng Biotechnology, vol. 2, No. 41, Oct. 6, 2014, 14 pages.
Menzella, "Comparison of two codon optimization strategies to enhance recombinant protein production in *Escherichia coli*", Microbial Cell Factories, vol. 10, No. 15, Mar. 1, 2011, 8 pages.
Novoa et al., "Speeding with control: codon usage, tRNAs, and ribosomes", Trends in Genetics, vol. 28, No. 11, Nov. 1, 2012, pp. 574-581.
PCT/US2015/067024, "International Preliminary Report on Patentability", dated Jul. 6, 2017, 9 pages.
PCT/US2015/067024, "International Search Report and Written Opinion", dated Apr. 21, 2016, 15 pages.
Plotkin et al., "Synonymous but not the same: the causes and consequences of codon bias", Nature Reviews Genetics, vol. 12, No. 1, Jan. 1, 2011, pp. 32-42.

*Primary Examiner* — G Steven Vanni
(74) *Attorney, Agent, or Firm* — Womble Bond Dickinson (US) LLP

(57) ABSTRACT

Methods for making a synthetic gene are provided. The methods find use in optimizing a candidate gene nucleic acid sequence for expression in a selected target expression system. The method identifies stable or retained sequences in the candidate gene nucleic acid sequence, identifies disallowed sequences, develops a statistical model based on a whole genome, a partial genome, or transcriptome sequences of the target expression system, generates an optimized candidate gene nucleic acid sequence for use in the target expression system, and makes a synthetic gene comprising the optimized candidate gene nucleic acid sequence. The method allows for optimization of the candidate gene nucleic acid sequence without removing certain stable or retained sequences. Rather, the activity of these sites is positionally modulated or inactivated through upstream and downstream modifications of codons and/or sequence patterns.

27 Claims, No Drawings
Specification includes a Sequence Listing.

OPTIMIZATION METHODS FOR MAKING A SYNTHETIC GENE

CROSS REFERENCE TO RELATED APPLICATION

This application claims the benefit of U.S. Provisional Application Ser. No. 62/095,367, filed Dec. 22, 2014; the contents of U.S. Provisional Application Ser. No. 62/095,367 are herein incorporated by reference in their entirety.

FIELD OF THE INVENTION

The invention relates to methods for making a synthetic gene that is optimized for expression in a target system.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named AgB007-PCT_SEQLIST.txt, created on Dec. 15, 2015, and having a size of 26.9 KB and is filed concurrently with the specification. The sequence listing contained in this ASCII formatted document is part of the specification and is herein incorporated by reference in its entirety.

BACKGROUND OF THE INVENTION

Optimization of a gene nucleic acid sequence is desirable in a number of circumstances. Genes that are cloned from one organism and then expressed in another of a different type (i.e., transgenes) often fail to express, or express poorly, in the target organism. Sequence optimization can correct this poor expression. In other cases, it may be desirable to alter or tune the expression of a specific gene in its native or recombinant context. Optimization may also be desirable not due to the target organism or system, but due to the technical manipulations used during the manipulation of a gene. One example is the removal of restriction endonuclease sites in order to simplify the construction of a vector for generation of transgenic organisms. In many cases, optimization removes known sequences that have a negative impact on gene expression in the target organism or expression system. For example, some sequences can cause message termination in transcribed RNA, cause folding of the nascent RNA that hinders translation, or can target transcribed RNA for degradation. Removing these sequences can improve expression by stabilizing the RNA message and allowing more abundant translation into protein. Other sequences may impact messages through other mechanisms, for example, by directing splicing or trafficking of the RNA or by changing the rates of protein transcription.

However, not all sequences and sequence patterns that govern protein production from a gene have been discovered, and sequences which were previously believed to govern protein production do not always do so in every circumstance. For example, some sequences and sequence patterns behave differently in different organisms or even in closely related organisms, or behave in other complex ways based on context or other poorly recognized variables. Therefore, it would be advantageous to develop further methods for gene optimization that account for potential regulatory effects of sequences and sequence patterns found in genes and in systems in which genes are heterologously expressed.

BRIEF SUMMARY OF THE INVENTION

Methods for making a synthetic gene are provided. The methods find use in optimizing a candidate gene nucleic acid sequence for expression in a selected target expression system by making the candidate more closely resemble genes in the target expression system. A target expression system can include, for example, a target organism or an in vitro expression system. The method identifies stable or retained sequences in the candidate gene nucleic acid sequence, identifies disallowed sequences, develops a statistical model based on a whole genome, a partial genome, or transcriptome sequences of the target expression system, generates an optimized candidate gene nucleic acid sequence for use in the target expression system, and makes a synthetic gene comprising the optimized candidate gene nucleic acid sequence. The method allows for optimization of the candidate gene nucleic acid sequence without removing certain stable or retained sequences. Rather, the activity of these sites is positionally modulated or inactivated through upstream and downstream modifications of regulatory codons and/or sequence patterns.

Embodiments of the invention include:

1) A method for making a synthetic gene, said method comprising:
   (a) identifying one or more stable or retained sequences in a candidate gene nucleic acid sequence;
   (b) identifying one or more disallowed sequences;
   (c) developing and/or using a statistical model based on a whole genome, a partial genome, or transcriptome sequences of a target expression system, wherein the statistical model comprises frequency of codon preference in the target expression system and frequency of nucleic acid sequences that are 5' and 3' to sequences that correspond to the one or more stable or retained sequences in the candidate gene nucleic acid sequence;
   (d) generating an optimized candidate gene nucleic acid sequence for use in the target expression system, wherein generating comprises:
      (i) modifying localized sequences in the candidate gene nucleic acid sequence that are 5' and/or 3' to the one or more stable or retained sequences, wherein the modifications are based on the statistical model and often do not include a preferred codon modification, and wherein the modifications optimize gene expression in the target expression system;
      (ii) optionally modifying additional loci throughout the candidate gene nucleic acid sequence based on the statistical model, wherein the modifications do not include the modification of one or more stable or retained sequences or previously modified sequences, and wherein the modifications optimize gene expression in the target expression system; and
      (iii) optionally, modifying the one or more disallowed sequences in the candidate gene nucleic acid sequence; and
   (e) making a synthetic gene comprising the optimized candidate gene nucleic acid sequence.
2) The method of embodiment 1, wherein the synthetic gene is incorporated into an expression cassette.
3) The method of embodiment 2, wherein the expression cassette is introduced into a host cell, and wherein the host cell expresses the synthetic gene.
4) The method of any preceding embodiment, wherein the target expression system comprises a target organism or a target in vitro expression system.

5) The method of any preceding embodiment, wherein the one or more stable or retained sequences comprise certain polyadenylation sites, termination sites, RNA destabilizing sites, ATTTA motifs, exon-intron splice site signals, transposon-like repeats, restriction enzyme recognition sites, sequences deleterious to gene expression, or any combination thereof.

6) The method of any preceding embodiment, wherein the one or more disallowed sequences comprise certain polyadenylation sites, termination sites, RNA destabilizing sites, ATTTA motifs, exon-intron splice site signals, transposon-like repeats, restriction enzyme recognition sites, sequences deleterious to gene expression, or any combination thereof.

7) The method of any preceding embodiment, wherein the one or more disallowed sequences are scored.

8) The method of any preceding embodiment, wherein selected subsets of the whole genome, the partial genome, or the transcriptome sequences are used for developing the statistical model.

9) The method of any preceding embodiment, wherein selected subsets of the whole genome, the partial genome, or the transcriptome sequences are weighted in the statistical model.

10) The method of any preceding embodiment, wherein the statistical model further comprises compositional patterns in the whole genome, the partial genome, or the transcriptome sequences of the target expression system.

11) The method of embodiment 10, wherein the compositional patterns are normalized.

12) The method of embodiment 10 or embodiment 11, wherein the compositional patterns comprise the GC-type content, or any combination thereof.

13) The method of any preceding embodiment, wherein the localized modifications of the candidate gene nucleic acid sequence comprise substitutions of one or more codons that are 5' to the one or more stable or retained sequences, 3' to the one or more stable or retained sequences, or a combination thereof.

14) The method of any preceding embodiment, wherein the localized modifications of the candidate gene nucleic acid sequence comprise substitutions of one or more sequence patterns that are 5' to the one or more stable or retained sequences, 3' to the one or more stable or retained sequences, or a combination thereof.

15) The method of any preceding embodiment, wherein the modifications of additional loci throughout the candidate gene nucleic acid sequence comprise modifications to all regularly spaced or defined loci, wherein the modifications do not include the one or more stable or retained sequences or previously modified sequences.

16) The method of any preceding embodiment, wherein the modifications of additional loci throughout the candidate gene nucleic acid sequence comprise localized modifications of the one or more disallowed sequences.

17) The method of any preceding embodiment, wherein the modifications of additional loci throughout the candidate gene nucleic acid sequence comprise one or more substitutions of codons that are present at corresponding positions in the target expression system.

18) The method of any preceding embodiment, wherein preferences for the modifications of localized sequences in the candidate gene nucleic acid sequence, and preferences for the modifications of additional loci throughout the candidate gene nucleic acid sequence, are based on:

(a) resemblance to sequences observed in corresponding positions in the target expression system or related loci in other genes;

(b) removal of the one or more disallowed sequences;

(c) preventing the introduction of the one or more disallowed sequences;

(d) preservation of the one or more stable or retained sequences;

(e) codon preference; or (f) any combination of (a) to (e).

19) The method of any preceding embodiment, wherein preferences for modifications of the candidate gene nucleic acid sequence are scored simultaneously with weighted scores or are scored in separate sub-steps.

20) The method of any preceding embodiment, wherein the frequency of codon preference in the target expression system determined by the statistical model is normalized.

21) The method of any preceding embodiment, wherein the candidate gene nucleic acid sequence and the optimized candidate gene nucleic acid sequence encode the same polypeptide.

22) The method of any one of embodiments 1-20, wherein the optimized candidate gene nucleic acid sequence encodes a modified polypeptide.

23) The method of any one of embodiments 1-20, wherein the optimized candidate gene nucleic acid sequence comprises one or more stable or retained sequences at a different position relative to their endogenous position(s) in the candidate gene nucleic acid sequence.

24) The method of any one of embodiments 1-20, wherein the optimized candidate gene nucleic acid sequence further comprises one or more substitutions that are not based on the statistical model.

DETAILED DESCRIPTION OF THE INVENTION

Methods for making a synthetic gene are provided. The methods find use in optimizing a candidate gene nucleic acid sequence for expression in a target expression system. A target expression system can include, for example, a target organism or an in vitro expression system.

The utility of changing codon usage while optimizing genes for use in heterologous expression or transgene systems is well known in the art (Novoa et al., *Trends in Genetics* (2012) Vol. 28(11):574-581; Plotkin et al. (*Nature Reviews. Genetics* (2011) Vol. 12(1):32-42). There are many patterns observed in codon bias and other compositional patterns in expressed genes that may have effects on translation, message longevity, and transcription (U.S. Pat. Nos. 5,380,831 and 5,436,391; Murray et al., *Nucleic Acids Res.* (1989) Vol. 17:477-498; Ji et al., *BMC Bioinformatics* (2007) Vol. 8(1):43; Graber et al. *PNAS* (1999) Vol. 96(24): 14055-14060). Matching these patterns in a k-mer framework has been used as a method of gene optimization (U.S. Pat. No. 8,175,813).

Additional sequence modifications are known to enhance gene expression in a cellular host. These include elimination of sequences encoding spurious polyadenylation signals, RNA destabilizing sites, termination signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Furthermore, others have reported that removing termination and polyadenylation signals (deleterious sites) can be critical (Proudfoot *Genes and Development* (2011) Vol.

25(17): 1770-1782); Shen *Nucleic Acids Research* (2008) Vol. 36(9): 3150-3161). The AATAAA motif is the canonical terminator for eukaryotes, but there are others that are thought to be signals of varying strength in different groups of eukaryotic organisms (Graber et al. *PNAS* (1999) Vol. 96(24):14055-14060). Some methods include the identification of specific polyadenylation and RNA destabilizing sequences that potentially act as termination sites in a gene sequence and their removal for optimization of the gene sequence. For example, Fischhoff et al. (U.S. Pat. No. 7,741,118) describes a method of gene optimization that can include that the number of select polyadenylation sequences (disclosed therein in Table II) is reduced in the optimized gene sequence.

However, the use of whole-genome and whole transcriptome sequencing, as well as mRNA transcriptional end sequencing, have allowed additional exploration of the composition of mature transcripts. The present invention has used such bioinformatic analysis and confirmed that there are patterns present in sequences flanking termination, RNA destabilizing, and polyadenylation sites, as well as other regions surrounding these presumed deleterious sites at various distances (Ji et al. *Journal of Computational and Theoretical Nanoscience* (2007) Vol. 4(1): 1365-1368) that can be preserved or utilized to preserve these deleterious sites in the synthetic gene construct. The presence of some presumed deleterious sites in computationally predicted and directly sequenced transcripts from target genomes suggest that the composition of these flanking and distant regions can strongly modulate the activity of these regions and override the effect of the presumed deleterious sequence. The optimized gene or sequence of the present invention more closely resembles a sequence from the target expression system. That is, the optimized gene or sequence has sequence characteristics or stretches of nucleotides that are characteristic of sequences in the target expression system.

Thus, the present method allows for optimization of a candidate gene nucleic acid sequence without removing certain stable or retained sequences. By "stable" or "retained" sequences is meant that such sequences are maintained in the gene construct that is made based on the method described herein. The sequences are maintained and those upstream or downstream flanking sequences of the stable or retained sequences are modified such that the target host tolerates and effectively transcribes that synthetic construct comprising such stable or retained sequences. As noted below, these modifications while retaining the amino acid sequence may not result in preferred codons being used in these flanking regions. The method can be applied to the optimization of any DNA or RNA sequence.

I. Overview

A method for making a synthetic gene is provided. The method comprises identifying one or more stable or retained sequences in a candidate gene nucleic acid sequence. As indicated above, such stable or retained sequences are those sequences that are to be preserved in the synthetic construct and may include polyadenylation sites and/or termination sites. The method further comprises identifying disallowed sequences. "Disallowed sequences" are those sequences that are not preserved or are removed in the final synthetic construct.

The methods of the invention employ a statistical model that is developed based on a whole genome, a partial genome, or transcriptome sequences of a target expression system. That is, the whole genome or target sequences are analyzed to determine which otherwise deleterious sequences are used and do not alter expression. Sequences flanking these otherwise deleterious sequences are analyzed to determine how to modify flanking regions of other deleterious sequences. Using the statistical model, an optimized candidate gene nucleic acid sequence is generated for use in the target expression system. The regions around retained sequences are modified to mimic or be more similar to the flanking regions found in the target expression system. The method further comprises making a synthetic gene comprising the optimized candidate gene nucleic acid sequence.

As used herein, "optimization" refers to modifications of a gene nucleic acid sequence that modulate the expression of the gene when expressed in a selected target expression system. In some embodiments, optimization of the gene results in enhanced expression of the synthetic gene when expressed by the target expression system. Expression of the optimized gene can be enhanced by at least 5%, 10%, 15%, 20%, 25%, 50%, 75%, 100%, 200%, 500%, 1000%, or more, when compared to the expression of the native gene in the target expression system under similar conditions. In some embodiments, a gene can be optimized to achieve a desired level of expression, higher or lower than the expression of the native gene in the target expression system under similar conditions.

As used herein, "modifying" or "modification" refers to a change in the candidate gene nucleic acid sequence that can include, for example, substitutions, deletions, truncations, and/or insertions. In preferred embodiments, modifications to the nucleic acid sequence, such as substitutions of codons or sequence patterns, or the removal of disallowed sequences, do not alter the encoded amino acid sequence.

As used herein, all polynucleotide sequences written using the nucleic acid standard notation of the International Union of Pure and Applied Chemistry (IUPAC, *Biochemistry* (1970) Vol. 9:4022-4027); adenine (A), thymine (T), guanine (G), and cytosine (C) are equivalent to the corresponding RNA polynucleotide sequences. Therefore, "T" (Thymine) in all sequences is equivalent to "U" (uracil). For example, the sequence AATAAA in a DNA coding strand would also indicate the corresponding mRNA sequence AAUAAA.

As used herein, the use of the term "DNA", "nucleic acid", or "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

As used herein, a "candidate gene nucleic acid sequence" optimized by the method can be any gene of interest and can encode any polypeptide of interest. Exemplary genes of interest that can be optimized by the method are further described elsewhere herein.

A "target expression system" refers to, without limitation, any in vivo or in vitro expression system that facilitates expression of the synthetic gene. In one embodiment, a target expression system can be a target organism, or cell or part thereof. Exemplary target organisms that can be employed by the method are further described elsewhere herein. In another embodiment, a target expression system can be any in vitro expression system known in the art that allows for cell-free recombinant expression of the synthetic gene. In vitro expression systems can support protein synthesis from DNA templates (transcription and translation) or from mRNA templates (translation only), and can be designed to accomplish transcription and translation steps as two separate sequential reactions or concurrently as one reaction.

The method identifies one or more stable or retained sequences in the candidate gene nucleic acid sequence. As used herein, "stable" or "retained" sequences refer to specific sequences, codons, or sequence patterns in the candidate gene nucleic acid sequence that are maintained (i.e., not modified) during the method. In some embodiments, a retained sequence can be a potential polyadenylation site or a potential termination site identified in the candidate gene. In other embodiments, a retained sequence can be any sequence that has been identified in the art that negatively impacts expression of the candidate in the target host. In other embodiments, a retained sequence may refer to a pattern that is desirable to preserve for use in further genetic manipulations, such as restriction sites for restriction enzyme cleavage or transposition sites in gene shuffling approaches. In other embodiments, a retained sequence may refer to a mRNA transport signal or a 5' capping signal. In particular embodiments, a retained sequence can comprise a polyadenylation site, termination site, RNA destabilizing site, ATTTA motif, exon-intron splice site signal, transposon-like repeat, restriction enzyme recognition site, a sequence deleterious to gene expression, or any combination thereof. Exemplary retained sequences are described in the Examples provided herein.

As described herein the activity or negative impact of a retained sequence can be regulated by sequences or sequence patterns found upstream and/or downstream in the candidate gene nucleic acid sequence. Thus, the activity of a retained sequence can be positionally modulated or inactivated according to the method by modifying the flanking regions that may include regulatory sequences or sequence patterns positioned 5' upstream to the retained sequence, 3' downstream to the retained sequence, or a combination thereof. Such regulatory sequences or sequence patterns may be positioned adjacent to a retained sequence, or may be positioned at a particular distance from the retained sequence.

The method further identifies any disallowed sequences that may be present in the candidate gene. As used herein, "disallowed sequences" refer to specific sequences or sequence patterns that are identified for removal or modification if present in the candidate gene nucleic acid sequence. Disallowed sequences can also be identified to ensure that they are not introduced into the candidate gene nucleic acid sequence during optimization. In one embodiment, a disallowed sequence may be an ATTTA motif. In another embodiment, a disallowed sequence can be a restriction endonuclease site. Modification or removal of restriction endonuclease sites can modulate gene expression in the target expression system and/or promote the incorporation and function of the synthetic gene in an expression cassette or recombinant vector where particular restriction endonuclease sites may be problematic. In further embodiments, a disallowed sequence can comprise polyadenylation sites, termination sites, RNA destabilizing sites, ATTTA motifs, exon-intron splice site signals, transposon-like repeats, other such well-characterized sequences that may be deleterious to gene expression, restriction enzyme recognition sites, exon-intron splice site signals, known transposon-like repeats, or known patterns with strong RNA secondary structures. Exemplary disallowed sequences are described in the Examples herein. In some embodiments, disallowed sequences identified by the method can be scored based on how critical it is that the sequences be removed from the candidate gene nucleic acid sequence, modified in the sequence, or prevented from being introduced into the sequence.

The statistical model of the method is developed in silico using, for example, a program code. An exemplary program code is provided in the Examples herein. The statistical model can be based on the whole genome, a partial genome, or transcriptome sequences of the selected target expression system. The statistical model is applied to the candidate gene nucleic acid sequence to determine codons, sequence patterns, and/or disallowed sequences that can be modified to optimize the gene for expression in the target expression system.

In some embodiments, selected subsets of the whole genome, the partial genome, or the transcriptome sequences can be used for developing the statistical model. In other embodiments, selected subsets of the whole genome, the partial genome, or the transcriptome sequences can be weighted when developing the statistical model. Selected and weighted subsets can correspond, for example, to a particular region of interest in the candidate gene nucleic acid sequence.

The statistical model comprises various classes of information derived from the genome and/or transcriptome sequence(s) of the target expression system. For example, the statistical model comprises the frequency of codon preference and/or sequence pattern preference in the target expression system. Codon and sequence pattern frequency in the target expression system can indicate if a particular codon or sequence pattern occurs at a normal rate, at a higher than normal rate, or at a lower than normal rate. This analysis can further indicate the frequency of disallowed sequences and their position in the genome and/or transcriptome of the target expression system. In some embodiments, the frequency of codon preference and/or sequence pattern preference can be normalized in the method. In some embodiments, this normalization may be to the expression level of the transcript or the resulting protein as determined by, for example transcriptomic and proteomic measurements. In other embodiments, this normalization may be based on codon biases in a transcript, position of the pattern in the transcript, or confidence in a predicted transcript prediction. In other embodiments, this normalization may be passed on a mathematical or statistical transform of the data, such as log-values, standard deviations from the mean, or relative to the predicted occurrence rate of a pattern based on target genome composition.

The statistical model further comprises the frequency of nucleic acid sequences that are 5' and 3' to sequences that correspond to the one or more retained sequences in the candidate gene nucleic acid sequence. This analysis by the statistical model can provide the sequence context around retained sequences in the target expression system. The method can analyze the frequency of nucleic acid sequences and/or codons that are directly adjacent to retained sequences or, alternatively, upstream and/or downstream of retained sequences at particular distances. In some embodiments, the method analyzes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more base pairs that are 0, 1, 2, 3, 4, 5, 6, 7, 8, 9, 10, 11, 12, 13, 14, 15, 16, 17, 18, 19, 20, 30, 40, 50, 60, or 70 or more base pairs 5' upstream and/or 3' downstream of a retained sequence for frequency of nucleic acid sequence patterns and/or codons. In some embodiments, the method involves analyzing about 5, about 6, about 7, about 8, about 9, about 10, about 11, up to about 12 base pairs immediately 5' upstream and/or 3' downstream of a retained sequence. After analyzing, modifications are made in some or all of these base pairs to mimic or more closely resemble the sequence context around retained sequences in the target expression system. In this manner, the representation of the inactivating sequences will be found in adequate numbers in the statistical model and the program implementing this approach is computationally tractable. The flanking regions in a candidate gene or sequence will be modified to comprise the same sequence context as is found in the target expression system both 5' and 3' to the retained sequence.

The model of the sequence context around retained sequences may, in some embodiments, be normalized. This normalization may be with respect to the frequency of occurrence of the retained sequence. In other embodiments, this normalization may be with respect to the expression level of the transcript or the resulting protein as determined by, for example, transcriptomic and proteomic measurements. In other embodiments, this normalization may be based on codon biases in a transcript, position of the pattern in the transcript, or confidence in a predicted transcript prediction. In other embodiments, this normalization may be passed on a mathematical or statistical transform of the data, such as log-values, standard deviations from the mean, or relative to the predicted occurrence rate of a pattern based on target genome composition.

In some embodiments, the statistical model can further comprise compositional or large-scale patterns that are present in the genome or transcriptome sequences of the target expression system. In one example, compositional or large-scale patterns can be the GC-type content of the genome or transcriptome sequences.

In further examples, compositional or large-scale patterns can be genomic region-specific skews in nucleotide content or codon usage, histone binding patterns, or DNA secondary structure. Compositional or large-scale patterns can be normalized in the method. In some embodiments, this normalization may be to the expression level of the transcript or the resulting protein as determined by, for example transcriptomic and proteomic measurements. In other embodiments, this normalization may be based on codon biases in a transcript, position of the pattern in the transcript, or confidence in a predicted transcript prediction. In further embodiments, this normalization may be passed on a mathematical or statistical transform of the data, such as log-values, standard deviations from the mean, or relative to the predicted occurrence rate of a pattern based on target genome composition.

The optimized candidate gene nucleic acid sequence is generated in the method by applying the statistical model to the candidate gene nucleic acid sequence. Modifications to the candidate gene nucleic acid sequence can be made in silico within sequence windows. Different parts of the statistical model can be applied concurrently or sequentially.

Generating the optimized candidate gene nucleic acid sequence comprises modifying localized sequences in the candidate gene nucleic acid sequence that are 5' and/or 3' to one or more retained sequences. These localized modifications are based on the statistical model and optimize expression of the synthetic gene in the target expression system. In one embodiment, localized modifications of the candidate gene nucleic acid sequence comprise substitutions of one or more codons that are 5' upstream to the one or more retained sequences, 3' downstream to the one or more retained sequences, or a combination thereof. In another embodiment, the localized modifications of the candidate gene nucleic acid sequence comprise substitutions of one or more sequence patterns that are 5' upstream to the one or more retained sequences, 3' downstream to the one or more retained sequences, or a combination thereof. In some embodiments, the localized modifications involve substituting a lesser preferred codon in the flanking region.

Generating the optimized candidate gene nucleic acid sequence further comprises optionally modifying additional loci throughout the candidate gene nucleic acid sequence based on the statistical model. Additional loci may be limited to specific regions or stretches of nucleotides. Such modifications do not include modifications to retained sequences or further modifications to previously modified sequences. The modifications optimize expression of the synthetic gene in the target expression system.

In one embodiment, the modifications of additional loci throughout the candidate gene nucleic acid sequence comprise modifications to all regularly spaced or defined loci. Such modifications generally include codon substitutions. Codon substitutions may incorporate codons that are present at corresponding positions in the target expression system at a higher frequency than other codons, as determined by the statistical model. In some embodiments, the frequency of each codon in the candidate gene nucleic acid sequence is compared to the frequency of codons at the corresponding positions in the target expression system. In some examples, the codon having the highest occurrence in the target expression system is substituted into the candidate gene nucleic acid sequence. Alternatively, a codon having a higher occurrence than normal, but not the highest occurrence, is substituted into the candidate gene nucleic acid sequence. Such substitutions can allow for optimization of gene expression at desired level in the target expression system.

In another embodiment, the modifications of additional loci throughout the candidate gene nucleic acid sequence comprise localized modifications of one or more disallowed sequences. Localized modifications of disallowed sequences can include, for example, making synonymous codon substitutions overlapping their positions, such that the disallowed sequences are changed while maintaining the native amino acid sequence.

Generating the optimized candidate gene nucleic acid sequence may further comprise modifying at least one of the one or more disallowed sequences in the candidate gene nucleic acid sequence.

When making modifications to localized sequences in the candidate gene nucleic acid sequence, or modifications of additional loci throughout the candidate gene nucleic acid sequence, the method can assign a preference to particular modifications based on a number of factors derived from the statistical model, the candidate gene nucleic acid sequence, and/or the genome or transcriptome sequence(s) of the target expression system. In one embodiment, preferences for modifications can be based on the resemblance of a codon or sequence pattern in the candidate gene nucleic acid sequence to sequences observed in corresponding positions in the target expression system or related loci in other genes. In another embodiment, preferences for modifications can be based on the removal of one or more disallowed sequences from the candidate gene nucleic acid sequence, or preventing the introduction of one or more disallowed sequences in the candidate gene nucleic acid sequence. In yet another embodiment, preferences for modifications can be based on the preservation of one or more retained sequences. In a further embodiment, preferences for modifications can be based on codon preferences observed in the genome or transcriptome of the target expression system.

Preferences for modifications of the candidate nucleic acid sequence can be scored. Scoring can be performed simultaneously with weighted scores. Alternatively, scoring can be performed in separate sub-steps.

Following in silico modifications, a synthetic gene is made that comprises the optimized gene nucleic acid sequence. The synthetic gene is optimized for expression in the selected target expression system. Optimization can include enhanced expression or, alternatively, expression at a desired level. The synthetic gene can be made, for example, by modifying the native nucleic acid sequence of the candidate gene. The candidate gene may be altered in various ways including nucleic acid substitutions, deletions, truncations, and insertions. Methods for such manipulations are generally known in the art. For example, methods for mutagenesis and nucleic acid alterations are well known in the art. Designed changes can be introduced by various means, such as oligonucleotide-mediated site-directed mutagenesis techniques. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein. The synthetic gene can also be made by de novo chemical synthesis of sequences or subsequences and subsequent assembly. See for example, Tian et al. (2004) *Nature* 432, 7020:1050-54.

In some embodiments, the synthetic gene may encode the same amino acid sequence as the native candidate gene nucleic acid sequence. In other embodiments, the synthetic gene may encode a modified polypeptide, resulting from one or more modifications to the candidate gene nucleic acid sequence. Some polypeptide modifications can be made that are based on the statistical model of the method, for example by changing one or more amino acids to remove patterns that are not representative of the statistical model of the target organism. Some modifications can be made that are not based on the statistical model of the method. Rather, modifications can be made, for example, to modulate the function of the encoded polypeptide.

The synthetic gene can be incorporated into an expression cassette designed for expression of the gene in the target expression system. Such expression cassettes may be further incorporated into appropriate recombinant DNA vectors. The method further comprises introduction of the expression cassette into a host cell. Upon introduction of the expression cassette, the host cell expresses the synthetic gene. Exemplary expression cassettes and host cells are described in further detail elsewhere herein.

Although the method is described in a particular order, it should not be construed that the method must be performed in the order set forth herein. The steps of the method may be performed in any order based on the desired outcome of the method, the candidate gene nucleic acid sequence, and/or the selected target expression system.

II. Target Genes of Interest

The candidate gene that is modified by the method can be any gene of interest, and can be derived from any prokaryotic or eukaryotic organism.

In some embodiments, the gene of interest can be desirable for heterologous expression in a plant. The gene may be plant-derived or may be derived from another organism. Such genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism, as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988)*J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

III. Expression Cassettes

The synthetic gene made by the method can be incorporated into an expression cassette for expression in a host, or host cell or part thereof. The expression cassette can be further incorporated into an appropriate recombinant vector. The expression cassette may include 5' and/or 3' regulatory sequences operably linked to a polynucleotide. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two polypeptide coding regions, by operably linked is intended that the coding regions are in the same reading frame. The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain selectable marker genes.

For example, the expression cassette may include in the 5'-3' direction of transcription, a transcriptional and translational initiation region (i.e., a promoter), a polynucleotide (i.e., the synthetic gene) encoding a polypeptide of interest (and optionally coding sequences for one or more linker peptides), and a transcriptional and translational termination region (i.e., termination region) functional in the host organism. The regulatory regions (i.e., promoters, transcriptional regulatory regions, and translational termination regions) and/or the coding sequence for the polypeptide of interest may be native/analogous to the host cell or to each other. Alternatively, the regulatory regions and/or the coding sequence for the polypeptide of interest may be heterologous to the host cell or to each other. As used herein, "heterologous" is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

A heterologous promoter, or the native promoter sequence for the polypeptide of interest, may be used. Such constructs can change the levels of polypeptide expression in the host, or cell or part thereof. Thus, the phenotype of the host, or cell or part thereof, can be altered.

The termination region may be native with the transcriptional initiation region, may be native with the operably linked coding sequence for the polypeptide of interest, may be native with the host, or may be derived from another source (i.e., foreign or heterologous) to the promoter, the coding sequence for the polypeptide of interest, the host, or any combination thereof. Selection of suitable termination regions is within the means of one of ordinary skill in the art. For plant hosts, convenient termination regions may include, but are not limited to, those available from the Ti-plasmid of *A. tumefaciens*, such as the octopine synthase and nopaline synthase termination regions. See also Guerineau et al. (1991)*Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165:233-238), MDMV leader (Maize Dwarf Mosaic Virus) (Kong et al. (1988) *Arch Virol* 143:1791-1799), and human immunoglobulin heavy-chain binding polypeptide (BiP) (Macejak et al. (1991) *Nature* 353:90-94); untranslated leader from the coat polypeptide mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The synthetic gene can be combined with constitutive, tissue-preferred, inducible, or other promoters for expression in the host organism. For example, suitable constitutive promoters for use in a plant host cell include, without limitation, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter, for example, a wound-inducible promoter. Wound-inducible promoters may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the present invention. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983)

EMBO J. 2:987-992); methotrexate (Herrera Estrella et al. (1983) Nature 303:209-213; and Meijer et al. (1991) Plant Mol. Biol. 16:807-820); streptomycin (Jones et al. (1987) Mol. Gen. Genet. 210:86-91); spectinomycin (Bretagne-Sagnard et al. (1996) Transgenic Res. 5:131-137); bleomycin (Hille et al. (1990) Plant Mol. Biol. 7:171-176); sulfonamide (Guerineau et al. (1990) Plant Mol. Biol. 15:127-136); bromoxynil (Stalker et al. (1988) Science 242:419-423); glyphosate (Shaw et al. (1986) Science 233:478-481; and U.S. application Ser. Nos. 10/004,357; and 10/427,692); phosphinothricin (DeBlock et al. (1987) EMBO J. 6:2513-2518). See generally, Yarranton (1992) Curr. Opin. Biotech. 3: 506-511; Christopherson et al. (1992) Proc. Natl. Acad. Sci. USA 89: 6314-6318; Yao et al. (1992) Cell 71: 63-72; Reznikoff (1992) Mol. Microbiol. 6: 2419-2422; Barkley et al. (1980) in The Operon, pp. 177-220; Hu et al. (1987) Cell 48: 555-566; Brown et al. (1987) Cell 49: 603-612; Figge et al. (1988) Cell 52: 713-722; Deuschle et al. (1989) Proc. Natl. Acad. Sci. USA 86: 5400-5404; Fuerst et al. (1989) Proc. Natl. Acad. Sci. USA 86: 2549-2553; Deuschle et al. (1990) Science 248: 480-483; Gossen (1993) Ph.D. Thesis, University of Heidelberg; Reines et al. (1993) Proc. Natl. Acad. Sci. USA 90: 1917-1921; Labow et al. (1990) Mol. Cell. Biol. 10: 3343-3356; Zambretti et al. (1992) Proc. Natl. Acad. Sci. USA 89: 3952-3956; Baim et al. (1991) Proc. Natl. Acad. Sci. USA 88: 5072-5076; Wyborski et al. (1991) Nucleic Acids Res. 19: 4647-4653; Hillenand-Wissman (1989) Topics Mol. Struc. Biol. 10: 143-162; Degenkolb et al. (1991) Antimicrob. Agents Chemother. 35: 1591-1595; Kleinschnidt et al. (1988) Biochemistry 27: 1094-1104; Bonin (1993) Ph.D. Thesis, University of Heidelberg; Gossen et al. (1992) Proc. Natl. Acad. Sci. USA 89: 5547-5551; Oliva et al. (1992) Antimicrob. Agents Chemother. 36: 913-919; Hlavka et al. (1985) Handbook of Experimental Pharmacology, Vol. 78 (Springer-Verlag, Berlin); and Gill et al. (1988) Nature 334: 721-724. Such disclosures are herein incorporated by reference.

The above list of selectable marker genes is not meant to be limiting. Any selectable marker gene can be used in the present invention.

IV. Host Cells and Methods of Producing Host Cells

Expression cassettes comprising a synthetic gene can be introduced into a host cell for expression in a host, or cell or part thereof. As used herein, a "host, or cell or part thereof" refers to any organism, or cell, or part of that organism, that can be used as a suitable host for expressing the synthetic gene. It is understood that such a phrase refers not only to the particular host, or cell or part thereof, but also to the progeny or potential progeny thereof. Because certain modifications may occur in succeeding generations due to either mutation or environmental influences, such progeny may not, in fact, be identical to the parent, but are still included within the scope of the phrase as used herein.

As used herein, "introducing" is intended to mean presenting to the host cell the synthetic gene, or the expression cassette comprising the synthetic gene, in such a manner that the synthetic gene gains access to the interior of a cell. The methods of the invention do not depend on a particular method for introducing a synthetic gene or expression cassette into a host cell, only that the synthetic gene or expression cassette gains access to the interior of at least one cell of the host. Methods for introducing a synthetic gene or an expression cassette into plants are known in the art including, but not limited to, stable transformation methods, transient transformation methods, and virus-mediated methods.

In one example, the synthetic gene is expressed in a prokaryotic host, or cell or part thereof, or a eukaryotic host, or cell or part thereof. In another example, the host is an invertebrate host, or cell or part thereof, or a vertebrate host, or cell or part thereof. In another example, the host, or cell or part thereof, may be, but is not limited to, a bacterium, a fungus, yeast, a nematode, an insect, a fish, a plant, an avian, an animal, or a mammal.

Mammalian hosts, or cells or parts thereof, that are suitable for expression of the synthetic gene are known to those of ordinary skill in the art, and may include, but are not limited to, hamsters, mice, rats, rabbits, cats, dogs, bovine, goats, cows, pigs, horses, sheep, monkeys, or chimpanzees. Mammalian cells or mammalian parts may also be derived from humans, and the selection of such cells or parts would be known to those of ordinary skill in the art.

The selection of suitable bacterial hosts for expression of a synthetic gene is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.).

The selection of suitable yeast hosts for expression of a synthetic gene is known to those of ordinary skill in the art, and may include, but is not limited to, ascosporogenous yeasts (Endomycetales), basidiosporogenous yeasts and yeast belonging to Fungi Imperfecti (Blastomycetes). When selecting yeast hosts for expression, suitable hosts may include those shown to have, inter alia, good secretion capacity, low proteolytic activity, and overall vigor. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md. Since the classification of yeast may change in the future, yeast shall be defined as described in Skinner et al., eds. 1980) Biology and Activities of Yeast (Soc. App. Bacteriol. Symp. Series No. 9).

The selection of suitable insect hosts for expression of a synthetic gene is known to those of ordinary skill in the art, and may include, but is not limited to, Aedes aegypti, Bombyx mori, Drosophila melanogaster, Spodoptera frugiperda, and Trichoplusia ni. Insect cells suitable for the expression of a synthetic gene include, but are not limited to, SF9 cells, and others also well known to those of ordinary skill in the art. In selecting insect hosts for expression, suitable hosts may include those shown to have, inter alia, good secretion capacity, low proteolytic activity, and overall robustness. Insect hosts are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.)

The selection of suitable plant hosts for expression of a synthetic gene is known to those of ordinary skill in the art. As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Progeny, variants, and mutants of the regenerated plants are also included, provided that these parts comprise the introduced polynucleotides.

In one example, any plant species may be utilized as a host, including, but not limited to, monocots and dicots. Examples of plant species of interest include, but are not limited to, corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables of interest include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tuhpa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers of interest include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, *magnolia*, maple, oak, poplar, red alder, redbud, royal *paulownia, sassafras*, sweetgum, sycamore, tupelo, willow, yellow-poplar.

In specific examples, the plants or cells, or parts thereof are crop plants (for example, corn, alfalfa, sunflower, *Brassica*, soybean, cotton, safflower, peanut, *sorghum*, wheat, millet, tobacco, sugarcane etc.).

Other plants of interest include turfgrasses such as, for example, annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); blue gramma (*Bouteloua gracilis*); buffalo grass (*Buchloe dactyloids*); sideoats gramma (*Bouteloua curtipendula*).

Plants of interest further include grain plants that provide seeds of interest, oil-seed plants, and leguminous plants. Seeds of interest include grain seeds, such as corn, wheat, barley, rice, *sorghum*, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

Methods for expressing a synthetic gene in a host, or cell or part thereof, are well known to those of ordinary skill in the art. Transformation of appropriate hosts with an expression cassette is accomplished by well-known methods. With regard to transformation of prokaryotic hosts, see, for example, Cohen et al. (1972) Proc. Natl. Acad. Sci. USA 69:2110 and Sambrook et al. (1989) Molecular Cloning, A Laboratory Manual, Cold Spring Harbor Laboratory, Cold Spring Harbor, N.Y. Transformation of yeast is described in Sherman et al. (1986) Methods In Yeast Genetics, A Laboratory Manual, Cold Spring Harbor, N.Y. The method of Beggs (1978) Nature 275:104-109 is also useful. With regard to vertebrates, reagents useful in transfecting such hosts, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast, bacteria, insect cells and vertebrate cells.

A successfully transformed host, or cell or part thereof, i.e., one that contains a synthetic gene, and which is expressing the encoded polypeptide, can be identified using well-known techniques. For example, cells resulting from the introduction of an expression cassette can be grown to produce the polypeptide encoded by the synthetic gene. Cells can be harvested and lysed, and their DNA content examined for the presence of the synthetic gene using a method such as that described by Southern (1975) J. Mol. Biol. 98:503; or Berent et al. (1985) Biotech. 3:208. Alternatively, the presence of the encoded polypeptide in the supernatant can be detected using antibodies and methods known to those of ordinary skill in the art.

In addition to directly assaying for the presence of recombinant DNA, successful transformation can be confirmed by well-known immunological methods when the recombinant DNA is capable of directing the expression of the encoded polypeptide. For example, cells successfully transformed with an expression vector produce polypeptides displaying appropriate antigenicity. Samples of cells suspected of being transformed may be harvested and assayed for the encoded polypeptide using suitable antibodies. For stable transfection of a host, or cell or part thereof, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host, or cell or part thereof, along with the gene of interest. For example, selectable markers may include those which confer resistance to drugs, such as G418, hygromycin, and methotrexate. A nucleic acid encoding a selectable marker can be introduced into a host, or cell or part thereof, on the same vector as that comprising the synthetic gene, or alternatively introduced on a separate vector. A host, or cell, or part thereof, that is stably transfected with the introduced nucleic acid can be identified by drug selection.

The present inventions now will be described more fully hereinafter with reference to the following examples, in which some, but not all embodiments of the inventions are exemplified. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL

Example 1: Program Code for Making Synthetic Genes

This example provides a summary of the method of making synthetic genes as well as a script written in the object-oriented Python programming language for use in developing and applying the statistical model described herein. Example input and output sequences for optimized synthetic genes are included in Examples 2 to 4. This example script was developed to run on the Python interpreter (version 2.7.3 and later versions available from the Python Software Foundation), calls BioPython libraries (version 1.63 and later versions available from BioPython), and executes programs from the EMBOSS software suite (version 6.5.7.0 and later versions available from EMBOSS).

Target Genome Analysis:
1. Retrieve coding sequence from all genes predicted from genome sequence of Glycine max and Zea mays from public database.
2. Check sequence for non-terminal stop codons, discard any sequences that contain them.
3. Remove 45BP from 3' end of each sequence.
4. For trimmed plant coding sequences, find sequences in Retained Sequences (Table 2) for potential inactivation.
    a. Compile frequency of occurrence of all regions to be positionally inactivated normalized to the number of occurrences of any pattern that has the same length.
    b. Compile frequency of occurrence of regions to be positionally inactivated and all possible upstream and all possible downstream 6 nucleotides regions normalized by the number of occurrences of the core region.

Synthetic Gene Optimization:
Sequences that may be preserved and positionally inactivated patterns (see e.g., Table 2) are in the "Retained Sequence List." Other patterns and restriction enzyme sites (REs) that may be removed include ATTA (SEQ ID NO: 2) and the "RE List" (see e.g., Table 1).
1. Settings and reference information
    a. Set region to consider around patterns (6 BP), target organism (location of following files specific to organism), and locations of other sequence files (input, output location, other lists indicated below).
    b. Load frequency of occurrence of regions with scores.
    c. Load frequency of occurrence of 6BP upstream or downstream from regions with scores.
    d. Load equivalent codons for bacteria to plant.
    e. Load codon usage for target organism.
    f. Load Retained Sequence List.
    g. Load "Remove List" including ATTTA (SEQ ID NO: 2) and other sequences to be removed.
    h. Load RE list and convert names to DNA patterns.
    i. Generate single list of Disallowed Sequences including Remove List and other sequences.
    j. Initiate a datastructure that is a list of sets, where each set is composed of one or more elements, each of which stores 3 nucleotide bases and a corresponding numerical score. In addition, the datastructure holds the DNA sequence of the original gene to be optimized.
2. Load DNA of gene to be optimized in datastructure.
    a. Read in and parse file of gene to be optimized.
    b. Check for valid coding of gene to be optimized.
    c. Load DNA sequence of gene to be optimized into datastructure.
    d. Expand datastructure to hold all possible alternative codons for each codon position.
3. Disallow codons in regions so as to preserve sequences that will later be positionally inactivated.
    a. Zero out scores.
    b. Find locations of all patterns in Retained Sequence List in initial DNA sequence and score.
    c. Merge pattern locations to define codon regions where patterns overlap.
    d. Remove all possible alternative codons in datastructure set at codon locations in regions to preserve pattern and maximize score.
4. Disallow codons in regions so as to avoid forming sequences in the Remove List that are in the original sequence.
    a. Find locations of all patterns in Disallowed Sequences including Remove List in initial DNA sequence and score.
    b. Merge pattern locations to define regions where pattern regions will overlap.
    c. Remove all possible alternative codons at codon locations in regions that result in the pattern to be removed.
5. Disallow codons in regions so as to positionally inactivate targeted sequences in the Retained Sequence List that are in the original sequence, if possible also remove RE sites in these regions.
    a. Find locations of all patterns in Retained Sequence List in initial DNA sequence and the 6BP surrounding these regions.
    b. Merge pattern locations to define regions where patterns and 6BP surrounding regions will overlap.

6. Disallow codons in regions so as to:
   a. avoid forming sequences in the Remove List that would be generated by optimizing;
   b. positionally inactivate sequences in the Retained Sequence list as best as possible that would be generated; and
   c. if possible, also remove RE sites in these regions
7. Disallow codons in regions so as to positionally inactivate targeted sequences in the Retained Sequence List that would be formed by optimizing codons, if possible also remove RE sites in these regions.
   a. Find locations of all patterns in Retained Sequence List in codon optimized remaining sequence.
   b. Merge pattern locations to define regions where patterns and 6BP surrounding regions will overlap.
8. Disallow codons in regions so as to:
   a. Avoid forming sequences in the Remove List that would be generated by optimizing; and
   b. if possible, also remove RE sites in these regions.
9. For all other regions, select best (top) codon for target plant.

Reporting/Writeout:
1. Report scores and regions during each step above.
2. Output final optimized DNA sequence Example Script:

Example 2: Making of a Synthetic Gene for Expression in Soybean

This example describes the use of the statistical model of the invention, and the example script of Example 1, for generating an optimized *Bacillus thuringiensis* Cry1A nucleic acid sequence for expression in soybean. The *Bacillus thuringiensis* Cry1Ac1 candidate gene nucleic acid sequence is shown below:

Candidate Gene: *Bacillus thuringiensis* Cry1Ac1

```
(SEQ ID NO: 1)
ATGGATAACAATCCGAACATCAATGAATGCATTCCTTATAATTGTTTAA
GTAACCCTGAAGTAGAAGTATTAGGTGGAGAAAGAATAGAAACTGGTTA
CACCCCAATCGATATTTCCTTGTCGCTAACGCAATTTCTTTTGAGTGAA
TTTGTTCCCGGTGCTGGATTTGTGTTAGGACTAGTTGATATAATATGGG
GAATTTTTGGTCCCTCTCAATGGGACGCATTTCTTGTACAAATTGAACA
GTTAATTAACCAAAGAATAGAAGAATTCGCTAGGAACCAAGCCATTTCT
AGATTAGAAGGACTAAGCAATCTTTATCAAATTTACGCAGAATCTTTTA
GAGAGTGGGAAGCAGATCCTACTAATCCAGCATTAAGAGAAGAGATGCG
TATTCAATTCAATGACATGAACAGTGCCCTTACAACCGCTATTCCTCTT
TTTGCAGTTCAAAATTATCAAGTTCCTCTTTTATCAGTATATGTTCAAG
CTGCAAATTTACATTTATCAGTTTTGAGAGATGTTTCAGTGTTTGGACA
AAGGTGGGGATTTGATGCCGCGACTATCAATAGTCGTTATAATGATTTA
ACTAGGCTTATTGGCAACTATACAGATTATGCTGTACGCTGGTACAATA
CGGGATTAGAACGTGTATGGGACCGGATTCTAGAGATTGGGTAAGGTA
TAATCAATTTAGAAGAGAATTAACACTAACTGTATTAGATATCGTTGCT
CTGTTCCCGAATTATGATAGTAGAAGATATCCAATTCGAACAGTTTCCC
AATTAACAAGAGAAATTTATACAAACCCAGTATTAGAAAATTTTGATGG
```

-continued
```
TAGTTTTCGAGGCTCGGCTCAGGGCATAGAAAGAAGTATTAGGAGTCCA
CATTTGATGGATATACTTAACAGTATAACCATCTATACGGATGCTCATA
GGGGTTATTATTATTGGTCAGGGCATCAAATAATGGCTTCTCCTGTAGG
GTTTTCGGGGCCAGAATTCACTTTTCCGCTATATGGAACTATGGGAAAT
GCAGCTCCACAACAACGTATTGTTGCTCAACTAGGTCAGGGCGTGTATA
GAACATTATCGTCCACTTTATATAGAAGACCTTTTAATATAGGGATAAA
TAATCAACAACTATCTGTTCTTGACGGGACAGAATTTGCTTATGGAACC
TCCTCAAATTTGCCATCCGCTGTATACAGAAAAAGCGGAACGGTAGATT
CGCTGGATGAAATACCGCCACAGAATAACAACGTGCCACCTAGGCAAGG
ATTTAGTCATCGATTAAGCCATGTTTCAATGTTTCGTTCAGGCTTTAGT
AATAGTAGTGTAAGTATAATAAGAGCTCCTATGTTCTCTTGGATACATC
GTAGTGCTGAATTTAATAATATAATTGCATCGGATAGTATTACTCAAAT
CCCTGCAGTGAAGGGAAACTTTCTTTTTAATGGTTCTGTAATTTCAGGA
CCAGGATTTACTGGTGGGGACTTAGTTAGATTAAATAGTAGTGGAAATA
ACATTCAGAATAGAGGGTATATTGAAGTTCCAATTCACTTCCCATCGAC
ATCTACCAGATATCGAGTTCGTGTACGGTATGCTTCTGTAACCCCGATT
CACCTCAACGTTAATTGGGGTAATTCATCCATTTTTTCCAATACAGTAC
CAGCTACAGCTACGTCATTAGATAATCTACAATCAAGTGATTTTGGTTA
TTTTGAAAGTGCCAATGCTTTTACATCTTCATTAGGTAATATAGTAGGT
GTTAGAAATTTTAGTGGGACTGCAGGAGTGATAATAGACAGATTTGAAT
TTATTCCAGTTACTGCAACACTCGAGGCTGAATATAATCTGGAAAGAGC
GCAGAAGGCGGTGAATGCGCTGTTTACGTCTACAAACCAACTAGGGCTA
AAAACAAATGTAACGGATTATCATATTGATCAAGTGTCCAATTTAGTTA
CGTATTTATCGGATGAATTTTGTCTGGATGAAAAGCGAGAATTGTCCGA
GAAAGTCAAACATGCGAAGCGACTCAGTGATGAACGCAATTTACTCCAA
GATTCAAATTTCAAAGACATTAATAGGCAACCAGAACGTGGGTGGGCG
GAAGTACAGGGATTACCATCCAAGGAGGGGATGACGTATTTAAAGAAAA
TTACGTCACACTATCAGGTACCTTTGATGAGTGCTATCCAACATATTTG
TATCAAAAAATCGATGAATCAAAATTAAAAGCCTTTACCCGTTATCAAT
TAAGAGGGTATATCGAAGATAGTCAAGACTTAGAAATCTATTTAATTCG
CTACAATGCAAAACATGAAACAGTAAATGTGCCAGGTACGGGTTCCTTA
TGGCCGCTTTCAGCCCAAAGTCCAATCGGAAAGTGTGGAGAGCCGAATC
GATGCGCGCCACACCTTGAATGGAATCCTGACTTAGATTGTTCGTGTAG
GGATGGAGAAAAGTGTGCCCATCATTCGCATCATTTCTCCTTAGACATT
GATGTAGGATGTACAGACTTAAATGAGGACCTAGGTGTATGGGTGATCT
TTAAGATTAAGACGCAAGATGGGCACGCAAGACTAGGGAATCTAGAGTT
TCTCGAAGAGAAACCATTAGTAGGAGAAGCGCTAGCTCGTGTGAAAAGA
GCGGAGAAAAATGGAGAGACAAACGTGAAAAATTGGAATGGGAAACAA
ATATCGTTTATAAAGAGGCAAAAGAATCTGTAGATGCTTTATTTGTAAA
CTCTCAATATGATCAATTACAAGCGGATACGAATATTGCCATGATTCAT
GCGGCAGATAAACGTGTTCATAGCATTCGAGAAGCTTATCTGCCTGAGC
```

-continued

```
TGTCTGTGATTCCGGGTGTCAATGCGGCTATTTTTGAAGAATTAGAAGG

GCGTATTTTCACTGCATTCTCCCTATATGATGCGAGAAATGTCATTAAA

AATGGTGATTTTAATAATGGCTTATCCTGCTGGAACGTGAAAGGGCATG

TAGATGTAGAAGAACAAAACAACCAACGTTCGGTCCTTGTTGTTCCGGA

ATGGGAAGCAGAAGTGTCACAAGAAGTTCGTGTCTGTCCGGGTCGTGGC

TATATCCTTCGTGTCACAGCGTACAAGGAGGGATATGGAGAAGGTTGCG

TAACCATTCATGAGATCGAGAACAATACAGACGAACTGAAGTTTAGCAA

CTGCGTAGAAGAGGAAATCTATCCAAATAACACGGTAACGTGTAATGAT

TATACTGTAAATCAAGAAGAATACGGAGGTGCGTACACTTCTCGTAATC

GAGGATATAACGAAGCTCCTTCCGTACCAGCTGATTATGCGTCAGTCTA

TGAAGAAAAATCGTATACAGATGGACGAAGAGAGAATCCTTGTGAATTT

AACAGAGGGTATAGGGATTACACGCCACTACCAGTTGGTTATGTGACAA

AAGAATTAGAATACTTCCCAGAAACCGATAAGGTATGGATTGAGATTGG

AGAAACGGAAGGAACATTTATCGTGGACAGCGTGGAATTACTCCTTATG

GAGGAATAG
```

The *Glycine max* target organism genome data and coding sequences were obtained via the BioMart system from the Phytozome 9 Genomes database. The final 45 base pairs were removed from the 3' end of all predicted coding sequences. Disallowed sequences were designated, including the ATTTA motif (SEQ ID NO:2) and select restriction endonuclease sites summarized in Table 1.

TABLE 1

| RE Site | Sequence | SEQ ID NO: |
|---|---|---|
| AatII | GACGTC | 3 |
| AscI | GGCGCGCC | 4 |
| BglII | AGATCT | 5 |
| BsrGI | TGTACA | 6 |
| ClaI | ATCGAT | 7 |
| EcoRI | GAATTC | 8 |
| HindIII | AAGCTT | 9 |
| KpnI | GGTACC | 10 |
| NcoI | CCATGG | 11 |
| NdeI | CATATG | 12 |
| NotI | GCGGCCGC | 13 |
| PstI | CTGCAG | 14 |
| PvuII | CAGCTG | 15 |
| SacI | GAGCTC | 16 |
| SalI | GTCGAC | 17 |
| SmaI | CCCGGG | 18 |
| SpeI | ACTAGT | 19 |
| XbaI | TCTAGA | 20 |

TABLE 1-continued

| RE Site | Sequence | SEQ ID NO: |
|---|---|---|
| XhoI | CTCGAG | 21 |
| XmaI | CCCGGG | 22 |
| XmnI | GAANNNNTTC | 23 |
| BsgI | GTGCAG and CTGCAC | 24 and 25 |
| BamHI | GGATCC | 26 |
| PacI | TTAATTAA | 27 |
| PmeI | GTTTAAAC | 28 |
| SwaI | ATTTAAAT | 29 |

Retained sequences, representing potential polyadenylation sequences that may be preserved and positionally inactivated, were designated and are summarized in Table 2.

TABLE 2

| Retained Sequence | SEQ ID NO: |
|---|---|
| ATTAAA | 30 |
| AATACA | 31 |
| AAGCAT | 32 |
| AACCAA | 33 |
| AATAAA | 34 |
| ATACTA | 35 |
| CATAAA | 36 |
| AATTAA | 37 |
| ATAAAA | 38 |
| ATACAT | 39 |
| ATTAAT | 40 |
| ATGAAA | 41 |
| ATATAA | 42 |
| AATCAA | 43 |
| AATAAT | 44 |
| AAAATA | 45 |

Following analysis of the *Glycine max* target organism genome data and coding sequences, and development and application of the statistical model of the invention to the *Bacillus thuringiensis* Cry1Ac1 candidate gene nucleic acid sequence, modifications of the *Bacillus thuringiensis* Cry1Ac1 sequence were made to generate an optimized sequence as shown below:

Cry1Ac1 Gene Optimized for Expression in *Glycine max*

(SEQ ID NO: 46)
```
TGGATAACAATCCTAATATCAATGAATGTATTCCTTATAATTGTTTGTC

TAATCCTGAAGTTGAAGTTTTGGGAGGAGAAAGAATTGAAACTGGATAT
```

ACTCCTATTGATATTTCTTTGTCTTTGACTCAATTTTTGTTGTCTGAAT
TTGTTCCTGGAGCTGGATTTGTTCTTGGATTGGTGGATATAATATGGGG
GATTTTTGGACCTTCTCAATGGGATGCTTTTTTGGTTCAAATTGAACAA
TTGATCAATCAAAGAATTGAAGAATTTGCAAGAAATCAAGCAATTTCAA
GATTGGAAGGATTGTCTAATTTGTATCAAATATATGCTGAATCTTTTAG
AGAATGGGAAGCTGATCCTACTAATCCTGCTTTGAGAGAAGAAATGAGG
ATTCAATTCAATGATATGAACAGTGCTTTGACTACTGCTATTCCTTTGT
TTGCTGTTCAAAATTATCAAGTTCCTTTGTTGTCTGTTTATGTTCAAGC
TGCTAATTTGCATTTGTCTGTTTTGAGAGATGTTTCTGTTTTTGGACAA
AGATGGGGATTTGATGCTGCTACTATCAATTCAAGATACAATGATTTGA
CTAGATTGATTGGAAATTATACTGATTATGCTGTTAGATGGTATAATAC
TGGATTGGAAAGAGTTTGGGGACCTGATTCAAGAGATTGGGTCAGATAC
AATCAATTCAGAAGAGAATTAACATTGACTGTTTTGGATATTGTTGCTT
TGTTTCCTAATTATGATTCAAGAAGATATCCTATTAGAACTGTTTCACA
ATTAACAAGAGAAATATATACAAATCCTGTTTTGGAAAATTTTGATGGA
TCTTTTAGAGGATCTGCTCAAGGAATTGAAAGAAGTATTAGAAGTCCTC
ATTTGATGGATATTCTCAATTCTATTACTATATATACTGATGCTCATAG
AGGATATTATTATTGGAGTGGACATCAAATAATGGCAAGTCCTGTTGGA
TTTTCTGGACCTGAGTTTACTTTTCCTTTGTATGGAACTATGGGAAATG
CTGCTCCTCAACAAAGAATTGTTGCTCAATTGGGACAAGGAGTTTATAG
AACTTTGTCTTCTACTTTGTATAGAAGACCTTTTAATATTGGAATCAAT
AATCAACAATTGTCTGTTTTGGATGGAACTGAATTTGCTTATGGAACTT
CTTCTAATTTGCCTTCTGCTGTTTATAGAAAGTCTGGAACTGTGGATTC
ATTGGATGAAATTCCCCCTCAAAACAATAATGTTCCTCCTAGACAAGGA
TTTTCTCATAGATTGTCTCATGTTTCTATGTTTAGAAGTGGATTTTCTA
ATTCTTCTGTTTCTATTATTAGAGCACCTATGTTTTCATGGATACATAG
AAGTGCAGAATTCAATAATATAATTGCAAGTGATTCTATTACTCAAATT
CCTGCTGTTAAGGGAAATTTTTTGTTTAATGGATCTGTTATTTCTGGAC
CTGGATTCACTGGAGGAGATTTGGTCAGATTAAATTCAAGTGGAAACAA
TATTCAAAACAGAGGATATATTGAAGTTCCTATTCATTTTCCTTCTACT
TCTACTAGATATAGAGTTAGAGTTAGATATGCTTCTGTTACTCCTATTC
ATTTGAATGTTAATTGGGGAAATTCTTCAATTTTTTCAAATACAGTTCC
TGCTACTGCTACTTCTTTGGACAATTTGCAATCAAGTGATTTTGGATAT
TTTGAATCTGCTAATGCTTTTACTTCTTCTTTGGGAAATATTGTTGGAG
TTAGAAATTTTTCTGGAACTGCTGGAGTTATTATTGATAGATTTGAATT
CATTCCTGTTACTGCTACATTGGAAGCAGAATACAATTTGGAAAGAGCA
CAAAAGGCTGTTAATGCTTTGTTTACATCAACAAATCAATTGGGGTTGA
AGACTAATGTTACTGATTATCATATTGATCAAGTTTCTAATTTGGTTAC
TTATTTGTCTGATGAATTTGTTTGGATGAAAAAGAGAATTGTCTGAA
AAGGTTAAACATGCTAAGAGATTGTCTGATGAGAGAAATTTGTTGCAAG
ATTCTAATTTCAAAGATATTAATAGACAACCTGAAAGAGGATGGGAGG
ATCTACTGGAATTACTATTCAAGGAGGAGATGATGTTTTCAAGGAAAAT
TATGTTACTTTGTCTGGAACTTTTGATGAATGTTATCCTACTTATTTGT
ATCAAAAAATTGATGAATCAAAATTAAAAGCATTTACAAGATATCAATT
AAGAGGATATATTGAAGATTCTCAAGATTTGGAAATATATTTGATTAGA
TACAATGCAAAACATGAAACTGTCAATGTTCCTGGAACTGGATCTTTGT
GGCCTTTGTCTGCTCAATCTCCTATTGGAAAGTGTGGAGAACCTAATAG
ATGTGCTCCTCATTTGGAATGGAATCCTGATTTGGATTGTTCTTGTAGA
GATGGAGAAAAGTGTGCTCATCATTCTCATCATTTTCTTTGGATATTG
ATGTTGGATGTACTGATTTGAATGAAGATTTGGGAGTTTGGGTTATTTT
TAAGATTAAGACTCAAGATGGACATGCTAGATTGGGAAATTTGGAATTT
TTGGAAGAAAAGCCTTTGGTTGGAGAGGCATTGGCTAGAGTTAAGAGAG
CTGAAAAGAAGTGGAGAGATAAGAGAGAAAAGTTGGAATGGGAAACTAA
TATTGTTTATAAGGAAGCTAAGGAATCTGTTGATGCTTTGTTTGTTAAT
TCTCAATATGATCAATTGCAAGCTGATACAAATATTGCTATGATTCATG
CTGCTGATAAGAGAGTTCATTCTATTAGAGAGGCATATTTGCCTGAATT
GTCTGTTATTCCTGGAGTTAATGCTGCTATTTTTGAAGAATTGGAAGGA
AGAATTTTTACTGCTTTTTCTTTGTATGATGCAAGAAATGTTATAAAAA
ATGGAGATTTCAATAATGGATTGTCTTGTTGGAATGTTAAGGGACATGT
TGATGTTGAAGAACAAAACAATCAAAGAAGTGTTTTGGTTGTTCCTGAA
TGGGAAGCTGAAGTTTCTCAAGAAGTTAGAGTTTGTCCTGGAAGAGGAT
ATATTTTGAGAGTTACTGCTTATAAGGAAGGATATGGAGAAGGATGTGT
TACTATTCACGAAATTGAAAACAATACAGATGAATTGAAGTTTTCTAAT
TGTGTTGAAGAAGAAATATATCCTAACAATACTGTTACTTGTAATGATT
ATACTGTCAATCAAGAAGAATATGGAGGAGCTTATACTTCAAGAAATCG
TGGATATAATGAAGCTCCTTCTGTTCCTGCTGATTATGCTTCTGTTTAT
GAAGAAAGTCTTATACTGATGGAAGAAGAGAAAATCCTTGTGAATTCA
ATAGAGGATATAGAGATTATACTCCTTTGCCTGTTGGATATGTTACTAA
GGAATTGGAATATTTTCCTGAAACTGATAAGGTTTGGATTGAAATTGGA
GAAACTGAAGGAACATTCATTGTTGATTCTGTTGAATTGTTGTTGATGG
AAGAATAG

A synthetic gene can be made using the optimized Cry1Ac1 gene nucleic acid sequence for expression in soybean.

Example 3: Making a Synthetic Gene for Expression in Soybean

This example describes the use of the statistical model of the invention, and the example script of Example 1, for generating an optimized β-Glucuronidase (GUS) nucleic acid sequence, derived from *Escherichia coli*, for expression in soybean. The *E. coli* GUS candidate gene nucleic acid sequence is shown below:

Candidate Gene: *E. coli* GUS (SEQ ID NO: 47)
ATGGTAGATCTGAGGAACCGACGACTCGTCCGTCCTGTAGAAACCCCAA
CCCGTGAAATCAAAAAACTCGACGGCCTGTGGGCATTCAGTCTGGATCG
CGAAAACTGTGGAATTGATCAGCGTTGGTGGGAAAGCGCGTTACAAGAA
AGCCGGGCAATTGCTGTGCCAGGCAGTTTTAACGATCAGTTCGCCGATG
CAGATATTCGTAATTATGCGGGCAACGTCTGGTATCAGCGCGAAGTCTT
TATACCGAAAGGTTGGGCAGGCCAGCGTATCGTGCTGCGTTTCGATGCG
GTCACTCATTACGGCAAAGTGTGGGTCAATAATCAGGAAGTGATGGAGC
ATCAGGGCGGCTATACGCCATTTGAAGCCGATGTCACGCCGTATGTTAT
TGCCGGGAAAGTGTACGTATCACCGTTTGTGTGAACAACGAACTGAAC
TGGCAGACTATCCCGCCGGGAATGGTGATTACCGACGAAAACGGCAAGA
AAAAGCAGTCTTACTTCCATGATTTCTTTAACTATGCCGGAATCCATCG
CAGCGTAATGCTCTACACCACGCCGAACACCTGGGTGGACGATATCACC
GTGGTGACGCATGTCGCGCAAGACTGTAACCACGCGTCTGTTGACTGGC
AGGTGGTGGCCAATGGTGATGTCAGCGTTGAACTGCGTGATGCGGATCA
ACAGGTGGTTGCAACTGGACAAGGCACTAGCGGGACTTTGCAAGTGGTG
AATCCGCACCTCTGGCAACCGGGTGAAGGTTATCTCTATGAACTCGAAG
TCACAGCCAAAAGCCAGACAGAGTCTGATATCTACCCGCTTCGCGTCGG
CATCCGGTCAGTGGCAGTGAAGGGCCAACAGTTCCTGATTAACCACAAA
CCGTTCTACTTTACTGGCTTTGGTCGTCATGAAGATGCGGACTTACGTG
GCAAAGGATTCGATAACGTGCTGATGGTGCACGACCACGCATTAATGGA
CTGGATTGGGGCCAACTCCTACCGTACCTCGCATTACCCTTACGCTGAA
GAGATGCTCGACTGGGCAGATGAACATGGCATCGTGGTGATTGATGAAA
CTGCTGCTGTCGGCTTTCAGCTGTCTTTAGGCATTGGTTTCGAAGCGGG
CAACAAGCCGAAAGAACTGTACAGCGAAGAGGCAGTCAACGGGGAAACT
CAGCAAGCGCACTTACAGGCGATTAAAGAGCTGATAGCGCGTGACAAAA
ACCACCCAAGCGTGGTGATGTGGAGTATTGCCAACGAACCGGATACCCG
TCCGCAAGGTGCACGGGAATATTTCGCGCCACTGGCGGAAGCAACGCGT
AAACTCGACCCGACGCGTCCGATCACCTGCGTCAATGTAATGTTCTGCG
ACGCTCACACCGATACCATCAGCGATCTCTTTGATGTGCTGTGCCTGAA
CCGTTATTACGGATGGTATGTCCAAAGCGGCGATTTGGAAACGGCAGAG
AAGGTACTGGAAAAAGAACTTCTGGCCTGGCAGGAGAAACTGCATCAGC
CGATTATCATCACCGAATACGGCGTGGATACGTTAGCCGGGCTGCACTC
AATGTACACCGACATGTGGAGTGAAGAGTATCAGTGTGCATGGCTGGAT
ATGTATCACCGCGTCTTTGATCGCGTCAGCGCCGTCGTCGGTGAACAGG
TATGGAATTTCGCCGATTTTGCGACCTCGCAAGGCATATTGCGCGTTGG
CGGTAACAAGAAAGGGATCTTCACTCGCGACCGCAAACCGAAGTCGGCG
GCTTTTCTGCTGCAAAAACGCTGGACTGGCATGAACTTCGGTGAAAAAC
CGCAGCAGGGAGGCAAACAAGCTAGCCACCACCACCACCACCACGTGTG
A The *Glycine max* target organism genome data and coding sequences were obtained via the BioMart system from the Phytozome 9 Genomes database. The final 45 base pairs were removed from the 3' end of all predicted coding sequences. Disallowed sequences were designated, including the ATTTA motif (SEQ ID NO:2) and select restriction endonuclease sites summarized above in Table 1. Retained sequences, representing potential polyadenylation sequences that may be preserved and positionally inactivated, were designated and are summarized above in Table 2.

Following analysis of the *Glycine max* target organism genome data and coding sequences, and development and application of the statistical model of the invention to the *E. coli* GUS candidate gene nucleic acid sequence, modifications of the GUS sequence were made to generate an optimized sequence as shown below:

GUS Gene Optimized for Expression in *Glycine max*

(SEQ ID NO: 48)
ATGGTTGATTTGAGAAATAGAAGATTGGTTAGACCTGTTGAAACTCCCA
CAAGAGAAATTAAAAAATTGGATGGATTGTGGGCTTTTTCTTTGGATAG
AGAAAATTGTGGAATTGATCAAAGATGGTGGGAATCTGCTTTGCAAGAA
TCTAGAGCTATTGCTGTTCCTGGATCTTTTAATGATCAATTTGCTGATG
CTGATATTAGAAATTATGCTGGAAATGTTTGGTATCAAAGAGAAGTTTT
TATTCCTAAGGGATGGGCTGGACAAAGAATTGTTTTGAGATTTGATGCT
GTTACTCATTATGGAAAAGTGTGGGTGAACAACCAAGAAGTTATGGAAC
ATCAAGGAGGATATACTCCTTTTGAAGCTGATGTTACTCCTTATGTTAT
TGCTGGAAAGTCTGTTAGAATTACTGTTTGTGTTAATAATGAATTGAAT
TGGCAAACTATTCCTCCTGGAATGGTTATTACTGATGAAAATGGAAAGA
AGAAGCAATCTTATTTTCATGATTTTTTTAATTATGCTGGAATTCATAG
ATCTGTTATGTTGTATACTACTCCTAATACTTGGGTTGATGATATTACT
GTTGTTACTCATGTTGCTCAAGATTGTAATCATGCTTCTGTTGATTGGC
AAGTTGTTGCTAATGGAGATGTTTCTGTTGAATTGAGAGATGCTGATCA
ACAAGTTGTTGCTACTGGACAAGGAACTTCTGGAACTTTGCAAGTTGTT
AATCCTCATTTGTGGCAACCTGGAGAAGGATATTTGTATGAATTGGAAG
TTACTGCTAAGTCTCAAACTGAATCTGATATTTATCCTTTGAGAGTTGG
AATTAGATCTGTTGCTGTTAAGGGACAACAATTTTTGATTAATCATAAG
CCTTTTTATTTTACTGGATTTGGAAGACATGAAGATGCTGATTTGAGAG
GAAAGGGATTTGATAATGTTTTGATGGTGCATGATCATGCATTAATGGA
TTGGATTGGAGCTAATTCTTATAGAACTTCTCATTATCCTTATGCTGAA
GAAATGTTGGATTGGGCTGATGAACATGGAATAGTGGTCATTGATGAAA
CTGCTGCGGTTGGATTTCAATTGTCTTTGGGAATTGGATTTGAAGCTGG
AAATAAGCCTAAGGAATTGTATTCTGAAGAAGCTGTTAATGGAGAAACT
CAACAAGCTCATCTCCAAGCCATAAAAGAATTGATTGCTAGAGATAAGA
ATCATCCTTCTGTTGTTATGTGGTCTATTGCTAATGAACCTGATACTAG
ACCTCAAGGAGCTAGAGAATATTTTGCTCCTTTGGCTGAAGCTACTAGA
AAGTTGGATCCTACTAGACCTATTACTTGTGTTAATGTTATGTTTTGTG

A

```
ATGCTCATACTGATACTATTTCTGATTTGTTTGATGTTTTGTGTTTGAA

TAGATATTATGGATGGTATGTTCAATCTGGAGATTTGGAAACTGCTGAA

AAGGTTTTGGAAAAGGAATTGTTGGCTTGGCAAGAAAAGTTGCATCAAC

CTATTATTATTACTGAATATGGAGTTGATACTTTGGCTGGATTGCATTC

TATGTATACTGATATGTGGTCTGAAGAATATCAATGTGCTTGGTTGGAT

ATGTATCATAGAGTTTTTGATAGAGTTTCTGCTGTTGTTGGAGAACAAG

TTTGGAATTTTGCTGATTTTGCTACTTCTCAAGGAATTTTGAGAGTTGG

AGGAAATAAGAAGGGAATTTTTACTAGAGATAGAAAGCCTAAGTCTGCT

GCTTTTTTGTTGCAAAAGAGATGGACTGGAATGAATTTTGGAGAAAAGC

CTCAACAAGGAGGAAAGCAAGCTTCTCATCATCATCATCATCATGTTTA

G
```

A synthetic gene can be made using the optimized GUS gene nucleic acid sequence for expression in soybean.

Example 4: Creation of a Synthetic Gene for Expression in Maize

This example describes the use of the statistical model of the invention, and the example script of Example 1, for generating an optimized *Bacillus thuringiensis* Cry1A nucleic acid sequence for expression in corn. The *Bacillus thuringiensis* Cry1Ac1 candidate gene nucleic acid sequence is the same as the sequence provided in Example 2.

The *Zea mays* target organism genome data and coding sequences were obtained via the BioMart system from the Phytozome 9 Genomes database. The final 45 base pairs were removed from the 3' end of all predicted coding sequences. Disallowed sequences were designated, including the ATTTA motif (SEQ ID NO:2) and select restriction endonuclease sites summarized above in Table 1. Retained sequences, representing potential polyadenylation sequences that may be preserved and positionally inactivated, were designated and are summarized above in Table 2.

Following analysis of the *Zea mays* target organism genome data and coding sequences, and development and application of the statistical model of the invention to the *Bacillus thuringiensis* Cry1Ac1 candidate gene nucleic acid sequence, modifications of the *Bacillus thuringiensis* Cry1Ac1 sequence were made to generate an optimized sequence as shown below:

Cry1Ac1 Gene Optimized for Expression in *Zea mays*

```
                                              (SEQ ID NO: 49)
ATGGACAACAACCCGAACATCAACGAGTGCATCCCGTACAACTGCCTGT

CCAACCCGGAGGTGGAGGTGCTGGCGGCGAGAGGATCGAGACCGGCTA

CACCCCGATCGACATCTCCCTGTCCCTGACCCAGTTCCTGCTGTCCGAG

TTCGTGCCGGGCGCCGGCTTCGTGCTGGGGCTGGTGGATATAATATGGG

GGATCTTCGGCCCGTCCCAGTGGGACGCCTTCCTGGTTCAGATCGAACA

ACTCATCAACCAAAGAATCGAGGAATTTGCCAGAAACCAAGCCATCTCC

AGGCTGGAGGGCCTGTCCAACCTGTACCAGATATACGCCGAGTCCTTCA

GGGAGTGGGAGGCCGACCCGACCAACCCGGCCCTGAGGGAGGAGATGAG

GATTCAGTTCAACGACATGAACTCCGCCCTGACCACCGCCATCCCGCTG

TTCGCCGTTCAGAACTACCAGGTGCCGCTGCTGTCCGTGTACGTTCAGG

CCGCCAACCTGCACCTGTCCGTGCTGAGGGACGTGTCCGTGTTCGGCCA

GAGGTGGGGCTTCGACGCCGCCACCATCAACTCCAGGTACAACGACCTG

ACCAGGCTGATCGGCAACTACACCGACTACGCCGTGAGGTGGTACAACA

CCGGCCTGGAGAGGGTGTGGGGCCCGGACTCCAGGGACTGGGTGCGATA

CAACCAATTCAGGAGAGAATTAACACTCACCGTGCTGGACATCGTGGCC

CTGTTCCCGAACTACGACTCCAGGAGATACCCCATCAGAACAGTTTCAC

AATTAACAAGAGAAATATACACCAACCCGGTGCTGGAGAACTTCGACGG

CTCCTTCAGGGGCTCCGCCCAGGGCATCGAGAGGTCCATCAGGTCCCCG

CACCTGATGGACATCCTGAACTCCATCACCATCTACACCGACGCCCACA

GGGGCTACTACTACTGGAGTGGACACCAAATAATGGCCAGCCCGGTGGG

CTTCTCCGGCCCGGAGTTCACCTTCCCGCTGTACGGCACAATGGGGAAC

GCCGCCCCGCAGCAGAGGATCGTGGCCCAACTGGGCCAGGGCGTATACA

GGACCCTGTCCTCCACCCTATACAGGAGGCCGTTCAACATTGGCATCAA

TAATCAACAACTGTCCGTGCTGGACGGCACCGAGTTCGCCTACGGCACC

TCCTCCAACCTGCCGTCCGCCGTATACAGGAAGTCCGGCACCGTGGATT

CACTGGATGAAATTCCACCGCAGAACAACGTGCCGCCGAGGCAGGG

ATTCAGCCACAGGCTGTCCCACGTGTCCATGTTCAGGTCCGGCTTCTCC

AACTCCTCCGTGTCCATCATCAGGGCCCCGATGTTTTCATGGATACATC

GAAGCGCAGAATTCAATAATATAATTGCCAGCGACTCCATCACCCAGAT

CCCGGCCGTGAAGGGCAACTTCCTGTTCAACGGCTCCGTGATCTCCGGA

CCTGGATTCACCGGCGGAGACCTGGTGCGATTAAATTCAAGCGGCAACA

ACATCCAGAACAGGGGCTACATCGAGGTGCCGATCCACTTCCCGTCCAC

CTCCACCAGGTACAGGGTGAGGGTGAGGTACGCCTCCGTGACCCCGATC

CACCTGAACGTGAACTGGGGCAACTCCTCAATTTTTTCAAATACAGTGC

CGGCCACCGCCACCTCCCTGGACAACCTGCAATCAAGCGATTTCGGCTA

CTTCGAGTCCGCCAACGCCTTCACCTCCTCCCTGGGCAACATCGTGGGC

GTGAGGAACTTCTCCGGCACCGCCGGCGTGATCATCGACAGGTTCGAAT

TCATCCCGGTGACCGCCACACTGGAGGCAGAATACAACCTGGAGAGGGC

CCAGAAGGCCGTGAACGCCCTGTTCACAAGCACAAACCAACTGGGGCTG

AAGACCAACGTGACCGACTACCACATCGACCAGGTGTCCAACCTGGTGA

CCTACCTGTCCGACGAATTCTGCCTGGATGAAAAGAGAGAGCTGTCCGA

GAAGGTGAAGCACGCCAAGAGGCTGTCCGACGAGAGGAACCTGTTGCAG

GACTCCAATTTCAAAGACATTAATCGACAGCCGGAGAGGGGCTGGGGCG

GCTCCACCGGCATCACCATCCAGGGCGGCGACGACGTTTTCAAGGAGAA

CTACGTGACCCTGTCCGGCACCTTCGACGAGTGCTACCCGACCTACCTG

TACCAGAAGATCGATGAATCAAAATTAAAGGCATTCACAAGATACCAAT

TAAGAGGATACATCGAGGACTCCCAGGACCTGGAGATATACCTGATCAG

GTACAATGCAAAACATGAAACAGTCAACGTGCCGGGCACCGGCTCCCTG

TGGCCGCTGTCCGCCCAGTCCCCGATCGGCAAGTGCGGCGAGCCGAACA
```

```
GGTGCGCCCCGCACCTGGAGTGGAACCCGGACCTGGACTGCTCATGCAG

GGACGGCGAGAAGTGCGCCCACCACTCCCACCACTTCTCCCTGGACATC

GACGTGGGCTGCACCGACCTGAACGAGGACCTGGGCGTGTGGGTGATCT

TCAAGATCAAGACCCAGGACGGCCACGCCAGGCTGGGCAACCTGGAGTT

CCTGGAGGAGAAGCCGCTGGTGGGCGAGGCCCTGGCCAGGGTGAAGAGG

GCCGAGAAGAAGTGGAGGGACAAGAGGGAGAAGCTGGAGTGGGAGACCA

ACATCGTATACAAGGAGGCCAAGGAGTCCGTGGACGCCCTGTTCGTGAA

CTCCCAGTACGACCAATTGCAGGCCGACACCAACATCGCCATGATCCAC

GCCGCCGACAAGAGGGTGCACTCCATCAGGGAGGCCTACCTGCCGGAGC

TGTCCGTGATTCCTGGCGTGAACGCCGCCATCTTCGAGGAGCTGGAGGG

CAGGATCTTCACCGCCTTCTCCCTGTACGACGCCAGAAATGTCATAAAA

AATGGCGATTTCAATAATGGACTGTCCTGCTGGAACGTGAAGGGCCACG

TGGACGTGGAAGAACAGAACAACCAAAGAAGCGTGCTGGTGGTGCCGGA

GTGGGAGGCCGAGGTGTCCCAGGAGGTGAGGGTGTGCCCTGGCAGGGGC

TACATCCTGAGGGTGACCGCCTACAAGGAGGGCTACGGCGAGGGCTGCG

TGACCATCCACGAGATCGAGAACAATACAGATGAGCTGAAGTTCTCCAA

CTGCGTGGAGGAGGAGATATACCCGAACAACACCGTGACCTGCAACGAC

TACACAGTCAACCAAGAAGAGTACGGCGGCGCCTACACCTCAAGAAACC

GTGGATATAATGAGGCCCCGTCCGTGCCGGCCGACTACGCCTCCGTGTA

CGAGGAGAAGTCCTACACCGACGGCAGGAGGGAGAACCCGTGCGAATTC

AACAGGGGCTACAGGGACTACACCCCGCTGCCGGTGGGCTACGTGACCA

AGGAGCTGGAGTACTTCCCGGAGACCGACAAGGTGTGGATCGAGATCGG

CGAGACCGAGGGCACATTCATCGTGGACTCCGTGGAGCTGCTGCTGATG

GAGGAGTAG
```

A synthetic gene can be made using the optimized Cry1Ac1 gene nucleic acid sequence for expression in corn.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for making a synthetic gene, said method comprising:
   (a) identifying one or more retained sequences in a candidate gene nucleic acid sequence, wherein the retained sequences are preserved in the synthetic gene;
   (b) identifying one or more disallowed sequences in the candidate gene nucleic acid sequence, wherein the disallowed sequences are not preserved in the synthetic gene;
   (c) using a statistical model based on a whole genome, a partial genome, or transcriptome sequences of a target expression system, wherein the statistical model comprises frequency of codon preference in the target expression system and frequency of nucleic acid sequences that are 5' and 3' to sequences that correspond to the one or more retained sequences in the candidate gene nucleic acid sequence;
   (d) generating an optimized candidate gene nucleic acid sequence for use in the target expression system, wherein generating comprises:
      (i) modifying localized sequences in the candidate gene nucleic acid sequence that are 5' and/or 3' to the one or more stable or retained sequences, wherein the modifications are based on the statistical model and often do not include a preferred codon modification or a lesser preferred codon modification based on the statistical model, and wherein the modifications optimize gene expression in the target expression system; and
   (e) making a synthetic gene comprising the optimized candidate gene nucleic acid sequence, wherein the synthetic gene comprises said retained sequences and does not comprise said disallowed sequences.

2. The method of claim 1, wherein the synthetic gene is incorporated into an expression cassette.

3. The method of claim 2, wherein the expression cassette is introduced into a host cell, and wherein the host cell expresses the synthetic gene.

4. The method of claim 1, wherein the target expression system comprises a target organism or a target in vitro expression system.

5. The method of claim 1, wherein the one or more retained sequences comprise polyadenylation sites, termination sites, RNA destabilizing sites, ATTTA motifs, exon-intron splice site signals, transposon-like repeats, restriction enzyme recognition sites, sequences deleterious to gene expression, or any combination thereof.

6. The method of claim 1, wherein the one or more disallowed sequences comprise polyadenylation sites, termination sites, RNA destabilizing sites, ATTTA motifs, exon-intron splice site signals, transposon-like repeats, restriction enzyme recognition sites, sequences deleterious to gene expression, or any combination thereof.

7. The method of claim 1, wherein the one or more disallowed sequences are scored.

8. The method of claim 1, wherein selected subsets of the whole genome, the partial genome, or the transcriptome sequences are used for developing the statistical model.

9. The method of claim 1, wherein selected subsets of the whole genome, the partial genome, or the transcriptome sequences are weighted in the statistical model.

10. The method of claim 1, wherein the statistical model further comprises compositional patterns in the whole genome, the partial genome, or the transcriptome sequences of the target expression system.

11. The method of claim 10, wherein the compositional patterns are normalized.

12. The method of claim 10, wherein the compositional patterns comprise the GC-type content.

13. The method of claim 1, wherein the localized modifications of the candidate gene nucleic acid sequence comprise substitutions of one or more codons that are 5' to the one or more retained sequences, 3' to the one or more retained sequences, or a combination thereof.

14. The method of claim 1, wherein the localized modifications of the candidate gene nucleic acid sequence comprise substitutions of one or more sequence patterns that are 5' to the one or more retained sequences, 3' to the one or more retained sequences, or a combination thereof.

15. The method of claim 1, wherein preferences for modifications of the candidate gene nucleic acid sequence are scored simultaneously with weighted scores or are scored in separate sub-steps.

16. The method of claim 1, wherein the frequency of codon preference in the target expression system is normalized.

17. The method of claim 1, wherein the candidate gene nucleic acid sequence and the optimized candidate gene nucleic acid sequence encode the same polypeptide.

18. The method of claim 1, wherein the optimized candidate gene nucleic acid sequence encodes a modified polypeptide.

19. The method of claim 1, wherein the optimized candidate gene nucleic acid sequence comprises one or more retained sequences at a different position relative to their endogenous position(s) in the candidate gene nucleic acid sequence.

20. The method of claim 1, wherein the optimized candidate gene nucleic acid sequence further comprises one or more substitutions that are not based on the statistical model.

21. The method of claim 1, wherein step (d) further comprises modifying the one or more disallowed sequences in the candidate gene nucleic acid sequence.

22. The method of claim 1, wherein the target expression system is a plant.

23. The method of claim 1, wherein step (d) further comprises modifying additional loci throughout the candidate gene nucleic acid sequence based on the statistical model, wherein the modifications do not include the modification of one or more retained sequences or previously modified sequences, and wherein the modifications optimize gene expression in the target expression system.

24. The method of claim 23, wherein preferences for the modifications of localized sequences in the candidate gene nucleic acid sequence, and preferences for the modifications of additional loci throughout the candidate gene nucleic acid sequence, are based on:
   (a) resemblance to sequences observed in corresponding positions in the target expression system or related loci in other genes;
   (b) removal of the one or more disallowed sequences;
   (c) preventing the introduction of the one or more disallowed sequences;
   (d) preservation of the one or more retained sequences;
   (e) codon preference; or
   (f) any combination of (a) to (e).

25. The method of claim 23, wherein the modifications of additional loci throughout the candidate gene nucleic acid sequence comprise modifications to all codons, wherein the modifications do not include the one or more retained sequences or previously modified sequences.

26. The method of claim 23, wherein the modifications of additional loci throughout the candidate gene nucleic acid sequence comprise localized modifications of the one or more disallowed sequences.

27. The method of claim 23, wherein the modifications of additional loci throughout the candidate gene nucleic acid sequence comprise one or more substitutions of codons that are present at corresponding positions in the target expression system.

* * * * *

SEQUENCE LISTING

<160> NUMBER OF SEQ ID NOS: 49

<210> SEQ ID NO 1
<211> LENGTH: 3537
<212> TYPE: DNA
<213> ORGANISM: Bacillus thuringiensis

<400> SEQUENCE: 1
atggataaca atccgaacat caatgaatgc attccttata attgtttaag taaccctgaa 60
gtagaagtat taggtggaga aagaatagaa actggttaca ccccaatcga tatttccttg 120
tcgctaacgc aatttctttt gagtgaattt gttcccggtg ctggatttgt gttaggacta 180
gttgatataa tatggggaat ttttggtccc tctcaatggg acgcatttct tgtacaaatt 240
gaacagttaa ttaaccaaag aatagaagaa ttcgctagga accaagccat ttctagatta 300
gaaggactaa gcaatcttta tcaaatttac gcagaatctt ttagagagtg ggaagcagat 360
cctactaatc cagcattaag agaagagatg cgtattcaat tcaatgacat gaacagtgcc 420
cttacaaccg ctattcctct tttgcagtt caaaattatc aagttcctct tttatcagta 480
tatgttcaag ctgcaaattt acatttatca gttttgagag atgtttcagt gtttggacaa 540
aggtggggat ttgatgccgc gactatcaat agtcgttata atgatttaac taggcttatt 600
ggcaactata cagattatgc tgtacgctgg tacaatacgg gattagaacg tgtatgggga 660
ccggattcta gagattgggt aaggtataat caatttagaa gagaattaac actaactgta 720
ttagatatcg ttgctctgtt cccgaattat gatagtagaa gatatccaat tcgaacagtt 780
tcccaattaa caagagaaat ttatacaaac ccagtattag aaaattttga tggtagtttt 840
cgaggctcgg ctcagggcat agaaagaagt attaggagtc cacatttgat ggatatactt 900

```
aacagtataa ccatctatac ggatgctcat aggggttatt attattggtc agggcatcaa    960
ataatggctt ctcctgtagg gttttcgggg ccagaattca cttttccgct atatggaact   1020
atgggaaatg cagctccaca caacgtatt gttgctcaac taggtcaggg cgtgtataga   1080
acattatcgt ccactttata tagaagacct tttaatatag gataaaataa tcaacaacta   1140
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attactcaaa tccctgcagt gaagggaaac   1440
tttcttttta atggttctgt aatttcagga ccaggattta ctggtgggga cttagttaga   1500
ttaaatagta gtggaaataa cattcagaat agagggtata ttgaagttcc aattcacttc   1560
ccatcgacat ctaccagata tcgagttcgt gtacggtatg cttctgtaac cccgattcac   1620
ctcaacgtta attggggtaa ttcatccatt ttttccaata cagtaccagc tacagctacg   1680
tcattagata atctacaatc aagtgatttt ggttattttg aaagtgccaa tgcttttaca   1740
tcttcattag gtaatatagt aggtgttaga aattttagtg ggactgcagg agtgataata   1800
gacagatttg aatttattcc agttactgca acactcgagg ctgaatataa tctggaaaga   1860
gcgcagaagg cggtgaatgc gctgtttacg tctacaaacc aactagggct aaaaacaaat   1920
gtaacggatt atcatattga tcaagtgtcc aatttagtta cgtatttatc ggatgaattt   1980
tgtctggatg aaaagcgaga attgtccgag aaagtcaaac atgcgaagcg actcagtgat   2040
gaacgcaatt tactccaaga ttcaaatttc aaagacatta ataggcaacc agaacgtggg   2100
tggggcggaa gtacagggat taccatccaa ggaggggatg acgtatttaa agaaaaattac  2160
gtcacactat caggtaccctt tgatgagtgc tatccaacat atttgtatca aaaaatcgat   2220
gaatcaaaat taaaagcctt tacccgttat caattaagag ggtatatcga agatagtcaa   2280
gacttagaaa tctatttaat tcgctacaat gcaaaacatg aaacagtaaa tgtgccaggt   2340
acgggttcct tatggccgct ttcagcccaa agtccaatcg gaaagtgtgg agagccgaat   2400
cgatgcgcgc cacaccttga atggaatcct gacttagatt gttcgtgtag ggatggagaa   2460
aagtgtgccc atcattcgca tcatttctcc ttagacattg atgtaggatg tacagactta   2520
aatgaggacc taggtgtatg ggtgatcttt aagattaaga cgcaagatgg gcacgcaaga   2580
ctagggaatc tagagtttct cgaagagaaa ccattagtag gagaagcgct agctcgtgtg   2640
aaaagagcgg agaaaaaatg gagagacaaa cgtgaaaaat tggaatggga aacaaatatc   2700
gtttataaag aggcaaaaga atctgtagat gctttatttg taaactctca atatgatcaa   2760
ttacaagcgg atacgaatat tgccatgatt catgcggcag ataaacgtgt tcatagcatt   2820
cgagaagctt atctgcctga gctgtctgtg attccgggtg tcaatgcggc tattttgaa    2880
gaattagaag ggcgtatttt cactgcattc tccctatatg atgcgagaaa tgtcattaaa   2940
aatggtgatt ttaataatgg cttatcctgc tggaacgtga agggcatgt agatgtagaa   3000
gaacaaaaca accaacgttc ggtccttgtt gttccggaat gggaagcaga agtgtcacaa   3060
gaagttcgtg tctgtccggg tcgtggctat atccttcgtg tcacagcgta caaggaggga   3120
tatggagaag gttgcgtaac cattcatgag atcgagaaca atacagacga actgaagttt   3180
agcaactgcg tagaagagga aatctatcca aataacacgg taacgtgtaa tgattatact   3240
gtaaatcaag aagaatacgg aggtgcgtac acttctcgta atcgaggata taacgaagct   3300
```

```
ccttccgtac cagctgatta tgcgtcagtc tatgaagaaa aatcgtatac agatggacga    3360
agagagaatc cttgtgaatt taacagaggg tatagggatt acacgccact accagttggt    3420
tatgtgacaa agaattaga atacttccca gaaaccgata aggtatggat tgagattgga    3480
gaaacggaag gaacatttat cgtggacagc gtggaattac tccttatgga ggaatag      3537
```

<210> SEQ ID NO 2
<211> LENGTH: 5
<212> TYPE: PRT
<213> ORGANISM: Artificial sequence
<220> FEATURE:
<223> OTHER INFORMATION: Synthesized

<400> SEQUENCE: 2

Ala Thr Thr Thr Ala
1               5

<210> SEQ ID NO 3
<211> LENGTH: 6
<212> TYPE: DNA
<213> ORGANISM: Artificial sequence
<220> FEATURE:
<223> OTHER INFORMATION: Synthesized

<400> SEQUENCE: 3 gacgtc                                                                    6

<210> SEQ ID NO 4
<211> LENGTH: 8
<212> TYPE: DNA
<213> ORGANISM: Artificial sequence
<220> FEATURE:
<223> OTHER INFORMATION: Synthesized

<400> SEQUENCE: 4 ggcgcgcc                                                                  8

<210> SEQ ID NO 5
<211> LENGTH: 6
<212> TYPE: DNA
<213> ORGANISM: Artificial sequence
<220> FEATURE:
<223> OTHER INFORMATION: Synthesized

<400> SEQUENCE: 5 agatct                                                                    6

<210> SEQ ID NO 6
<211> LENGTH: 6
<212> TYPE: DNA
<213> ORGANISM: Artificial sequence
<220> FEATURE:
<223> OTHER INFORMATION: Synthesized

<400> SEQUENCE: 6 tgtaca                                                                    6

<210> SEQ ID NO 7
<211> LENGTH: 6
<212> TYPE: DNA
<213> ORGANISM: Artificial Sequence
<220> FEATURE:
<223> OTHER INFORMATION: Synthesized

<400> SEQUENCE: 7

```
atcgat                                                          6

<210> SEQ ID NO 8
<211> LENGTH: 6
<212> TYPE: DNA
<213> ORGANISM: Artificial Sequence
<220> FEATURE:
<223> OTHER INFORMATION: Synthesized

<400> SEQUENCE: 8 gaattc                                                          6

<210> SEQ ID NO 9
<211> LENGTH: 6
<212> TYPE: DNA
<213> ORGANISM: Artificial sequence
<220> FEATURE:
<223> OTHER INFORMATION: Synthesized

<400> SEQUENCE: 9 aagctt                                                          6

<210> SEQ ID NO 10
<211> LENGTH: 6
<212> TYPE: DNA
<213> ORGANISM: Artificial Sequence
<220> FEATURE:
<223> OTHER INFORMATION: Synthesized

<400> SEQUENCE: 10 ggtacc                                                          6

<210> SEQ ID NO 11
<211> LENGTH: 6
<212> TYPE: DNA
<213> ORGANISM: Artificial Sequence
<220> FEATURE:
<223> OTHER INFORMATION: Synthesized

<400> SEQUENCE: 11 ccatgg                                                          6

<210> SEQ ID NO 12
<211> LENGTH: 6
<212> TYPE: DNA
<213> ORGANISM: Artificial Sequence
<220> FEATURE:
<223> OTHER INFORMATION: Synthesized

<400> SEQUENCE: 12 catatg                                                          6

<210> SEQ ID NO 13
<211> LENGTH: 8
<212> TYPE: DNA
<213> ORGANISM: Artificial Sequence
<220> FEATURE:
<223> OTHER INFORMATION: Synthesized

<400> SEQUENCE: 13 gcggccgc                                                        8

<210> SEQ ID NO 14
<211> LENGTH: 6
<212> TYPE: DNA
```

```
<213> ORGANISM: Artificial Sequence
<220> FEATURE:
<223> OTHER INFORMATION: Synthesized

<400> SEQUENCE: 14 ctgcag                                                              6

<210> SEQ ID NO 15
<211> LENGTH: 6
<212> TYPE: DNA
<213> ORGANISM: Artificial Sequence
<220> FEATURE:
<223> OTHER INFORMATION: Synthesized

<400> SEQUENCE: 15 cagctg                                                              6

<210> SEQ ID NO 16
<211> LENGTH: 6
<212> TYPE: DNA
<213> ORGANISM: Artificial Sequence
<220> FEATURE:
<223> OTHER INFORMATION: Synthesized

<400> SEQUENCE: 16 gagctc                                                              6

<210> SEQ ID NO 17
<211> LENGTH: 6
<212> TYPE: DNA
<213> ORGANISM: Artificial Sequence
<220> FEATURE:
<223> OTHER INFORMATION: Synthesized

<400> SEQUENCE: 17 gtcgac                                                              6

<210> SEQ ID NO 18
<211> LENGTH: 6
<212> TYPE: DNA
<213> ORGANISM: Artificial Sequence
<220> FEATURE:
<223> OTHER INFORMATION: Synthesized

<400> SEQUENCE: 18 cccggg                                                              6

<210> SEQ ID NO 19
<211> LENGTH: 6
<212> TYPE: DNA
<213> ORGANISM: Artificial Sequence
<220> FEATURE:
<223> OTHER INFORMATION: Synthesized

<400> SEQUENCE: 19 actagt                                                              6

<210> SEQ ID NO 20
<211> LENGTH: 6
<212> TYPE: DNA
<213> ORGANISM: Artificial Sequence
<220> FEATURE:
<223> OTHER INFORMATION: Synthesized

<400> SEQUENCE: 20 tctaga                                                              6
```

-continued

<210> SEQ ID NO 21
<211> LENGTH: 6
<212> TYPE: DNA
<213> ORGANISM: Artificial Sequence
<220> FEATURE:
<223> OTHER INFORMATION: Synthesized

<400> SEQUENCE: 21 ctcgag                                                                    6

<210> SEQ ID NO 22
<211> LENGTH: 6
<212> TYPE: DNA
<213> ORGANISM: Artificial Sequence
<220> FEATURE:
<223> OTHER INFORMATION: Synthesized

<400> SEQUENCE: 22 cccggg                                                                    6

<210> SEQ ID NO 23
<211> LENGTH: 10
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(7)
<223> OTHER INFORMATION: n=A,T,C, or G

<400> SEQUENCE: 23 gaannnnttc                                                               10

<210> SEQ ID NO 24
<211> LENGTH: 6
<212> TYPE: DNA
<213> ORGANISM: Artificial Sequence
<220> FEATURE:
<223> OTHER INFORMATION: Synthesized

<400> SEQUENCE: 24 gtgcag                                                                    6

<210> SEQ ID NO 25
<211> LENGTH: 6
<212> TYPE: DNA
<213> ORGANISM: Artificial Sequence
<220> FEATURE:
<223> OTHER INFORMATION: Synthesized

<400> SEQUENCE: 25 ctgcac                                                                    6

<210> SEQ ID NO 26
<211> LENGTH: 6
<212> TYPE: DNA
<213> ORGANISM: Artificial Sequence
<220> FEATURE:
<223> OTHER INFORMATION: Synthesized

<400> SEQUENCE: 26 ggatcc                                                                    6

<210> SEQ ID NO 27

```
<211> LENGTH: 8
<212> TYPE: DNA
<213> ORGANISM: Artificial Sequence
<220> FEATURE:
<223> OTHER INFORMATION: Synthesized

<400> SEQUENCE: 27 ttaattaa                                                                   8

<210> SEQ ID NO 28
<211> LENGTH: 8
<212> TYPE: DNA
<213> ORGANISM: Artificial Sequence
<220> FEATURE:
<223> OTHER INFORMATION: Synthesized

<400> SEQUENCE: 28 gtttaaac                                                                   8

<210> SEQ ID NO 29
<211> LENGTH: 8
<212> TYPE: DNA
<213> ORGANISM: Artificial Sequence
<220> FEATURE:
<223> OTHER INFORMATION: Synthesized

<400> SEQUENCE: 29 atttaaat                                                                   8

<210> SEQ ID NO 30
<211> LENGTH: 6
<212> TYPE: DNA
<213> ORGANISM: Artificial Sequence
<220> FEATURE:
<223> OTHER INFORMATION: Synthesized

<400> SEQUENCE: 30 attaaa                                                                     6

<210> SEQ ID NO 31
<211> LENGTH: 6
<212> TYPE: DNA
<213> ORGANISM: Artificial Sequence
<220> FEATURE:
<223> OTHER INFORMATION: Synthesized

<400> SEQUENCE: 31 aataca                                                                     6

<210> SEQ ID NO 32
<211> LENGTH: 6
<212> TYPE: DNA
<213> ORGANISM: Artificial Sequence
<220> FEATURE:
<223> OTHER INFORMATION: Synthesized

<400> SEQUENCE: 32 aagcat                                                                     6

<210> SEQ ID NO 33
<211> LENGTH: 6
<212> TYPE: DNA
<213> ORGANISM: Artificial Sequence
<220> FEATURE:
<223> OTHER INFORMATION: Synthesized

<400> SEQUENCE: 33
```

```
aaccaa                                                              6

<210> SEQ ID NO 34
<211> LENGTH: 6
<212> TYPE: DNA
<213> ORGANISM: Artificial Sequence
<220> FEATURE:
<223> OTHER INFORMATION: Synthesized

<400> SEQUENCE: 34 aataaa                                                              6

<210> SEQ ID NO 35
<211> LENGTH: 6
<212> TYPE: DNA
<213> ORGANISM: Artificial Sequence
<220> FEATURE:
<223> OTHER INFORMATION: Synthesized

<400> SEQUENCE: 35 atacta                                                              6

<210> SEQ ID NO 36
<211> LENGTH: 6
<212> TYPE: DNA
<213> ORGANISM: Artificial Sequence
<220> FEATURE:
<223> OTHER INFORMATION: Synthesized

<400> SEQUENCE: 36 cataaa                                                              6

<210> SEQ ID NO 37
<211> LENGTH: 6
<212> TYPE: DNA
<213> ORGANISM: Artificial Sequence
<220> FEATURE:
<223> OTHER INFORMATION: Synthesized

<400> SEQUENCE: 37 aattaa                                                              6

<210> SEQ ID NO 38
<211> LENGTH: 6
<212> TYPE: DNA
<213> ORGANISM: Artificial Sequence
<220> FEATURE:
<223> OTHER INFORMATION: Synthesized

<400> SEQUENCE: 38 ataaaa                                                              6

<210> SEQ ID NO 39
<211> LENGTH: 6
<212> TYPE: DNA
<213> ORGANISM: Artificial Sequence
<220> FEATURE:
<223> OTHER INFORMATION: Synthesized

<400> SEQUENCE: 39 atacat                                                              6

<210> SEQ ID NO 40
<211> LENGTH: 6
<212> TYPE: DNA
```

<213> ORGANISM: Artificial Sequence
<220> FEATURE:
<223> OTHER INFORMATION: Synthesized

<400> SEQUENCE: 40 attaat                                                                  6

<210> SEQ ID NO 41
<211> LENGTH: 6
<212> TYPE: DNA
<213> ORGANISM: Artificial Sequence
<220> FEATURE:
<223> OTHER INFORMATION: Synthesized

<400> SEQUENCE: 41 atgaaa                                                                  6

<210> SEQ ID NO 42
<211> LENGTH: 6
<212> TYPE: DNA
<213> ORGANISM: Artificial Sequence
<220> FEATURE:
<223> OTHER INFORMATION: Synthesized

<400> SEQUENCE: 42 atataa                                                                  6

<210> SEQ ID NO 43
<211> LENGTH: 6
<212> TYPE: DNA
<213> ORGANISM: Artificial Sequence
<220> FEATURE:
<223> OTHER INFORMATION: Synthesized

<400> SEQUENCE: 43 aatcaa                                                                  6

<210> SEQ ID NO 44
<211> LENGTH: 6
<212> TYPE: DNA
<213> ORGANISM: Artificial Sequence
<220> FEATURE:
<223> OTHER INFORMATION: Synthesized

<400> SEQUENCE: 44 aataat                                                                  6

<210> SEQ ID NO 45
<211> LENGTH: 6
<212> TYPE: DNA
<213> ORGANISM: Artificial Sequence
<220> FEATURE:
<223> OTHER INFORMATION: Synthesized

<400> SEQUENCE: 45 aaaata                                                                  6

<210> SEQ ID NO 46
<211> LENGTH: 3537
<212> TYPE: DNA
<213> ORGANISM: Artificial Sequence
<220> FEATURE:
<223> OTHER INFORMATION: Synthesized

<400> SEQUENCE: 46
atggataaca atcctaatat caatgaatgt attccttata attgtttgtc taatcctgaa      60

```
gttgaagttt tgggaggaga aagaattgaa actggatata ctcctattga tatttctttg      120
tctttgactc aattttttgtt gtctgaattt gttcctggag ctggatttgt tcttggattg     180
gtggatataa tatgggggat ttttggacct tctcaatggg atgcttttt ggttcaaatt      240 gaacaattga tcaatcaaag aattgaagaa tttgcaagaa atcaagcaat ttcaagattg     300
gaaggattgt ctaatttgta tcaaatatat gctgaatctt ttagagaatg ggaagctgat     360
cctactaatc ctgctttgag agaagaaatg aggattcaat tcaatgatat gaacagtgct     420
ttgactactg ctattccttt gtttgctgtt caaaattatc aagttccttt gttgtctgtt     480
tatgttcaag ctgctaattt gcatttgtct gttttgagag atgtttctgt ttttggacaa     540
agatggggat tgatgctgc tactatcaat tcaagataca atgatttgac tagattgatt      600
ggaaattata ctgattatgc tgttagatgg tataatactg gattggaaag agtttgggga     660
cctgattcaa gagattgggt cagatacaat caattcagaa gagaattaac attgactgtt     720
ttggatattg ttgctttgtt tcctaattat gattcaagaa gatatcctat tagaactgtt     780
tcacaattaa caagagaaat atatacaaat cctgttttgg aaaattttga tggatctttt     840
agaggatctg ctcaaggaat tgaaagaagt attagaagtc ctcatttgat ggatattctc     900
aattctatta ctatatatac tgatgctcat agaggatatt attattggag tggacatcaa     960
ataatggcaa gtcctgttgg attttctgga cctgagttta cttttccttt gtatggaact     1020
atgggaaatg ctgctcctca acaaagaatt gttgctcaat gggacaagg agtttataga      1080 actttgtctt ctactttgta tagaagacct tttaatattg gaatcaataa tcaacaattg     1140
tctgttttgg atggaactga atttgcttat ggaacttctt ctaatttgcc ttctgctgtt     1200
tatagaaagt ctggaactgt ggattcattg gatgaaattc cccctcaaaa caataatgtt     1260
cctcctagac aaggattttc tcatagattg tctcatgttt ctatgtttag aagtggatt      1320 tctaattctt ctgttttctat tattagagca cctatgtttt catggataca tagaagtgca    1380
gaattcaata atataattgc aagtgattct attactcaaa ttcctgctgt taagggaaat     1440 ttttgtta atggatctgt tatttctgga cctggattca ctggaggaga tttggtcaga       1500
ttaaattcaa gtggaaacaa tattcaaaac agaggatata ttgaagttcc tattcatttt     1560
ccttctactt ctactagata tagagttaga gttagatatg cttctgttac tcctattcat     1620
ttgaatgtta attggggaaa tcttcaatt ttttcaaata cagttcctgc tactgctact      1680
tctttggaca atttgcaatc aagtgatttt ggatatttg aatctgctaa tgcttttact      1740 tcttcttttgg aaatattgt tggagttaga aatttttctg gaactgctgg agttattatt     1800
gatagatttg aattcattcc tgttactgct acattggaag cagaatacaa tttggaaaga    1860
gcacaaaagg ctgttaatgc tttgtttaca tcaacaaatc aattgggttt gaagactaat    1920
gttactgatt atcatattga tcaagtttct aatttggtta cttatttgtc tgatgaattt    1980
tgtttggatg aaaaagaga attgtctgaa aaggttaaac atgctaagag attgtctgat    2040
gagagaaatt tgttgcaaga ttctaatttc aaagatatta atagacaacc tgaaagagga    2100
tggggaggat ctactggaat tactattcaa ggaggagatg atgttttcaa ggaaaattat    2160
gttactttgt ctgaacttt tgatgaatgt atcctactct atttgtatca aaaaattgat    2220
gaatcaaaat taaaagcatt tacaagatat caattaagag gatatattga agattctcaa    2280
gatttggaaa tatatttgat tagatacaat gcaaaacatg aaactgtcaa tgttcctgga    2340
actggatctt tgtggccttt gtctgctcaa tctcctattg gaaagtgtgg agaacctaat    2400
```

| | |
|---|---|
| agatgtgctc ctcatttgga atggaatcct gatttggatt gttcttgtag agatggagaa | 2460 |
| aagtgtgctc atcattctca tcatttttct ttggatattg atgttggatg tactgatttg | 2520 |
| aatgaagatt tgggagtttg ggttattttt aagattaaga ctcaagatgg acatgctaga | 2580 |
| ttgggaaatt tggaattttt ggaagaaaag cctttggttg gagaggcatt ggctagagtt | 2640 |
| aagagagctg aaaagaagtg gagagataag agagaaaagt tggaatggga aactaatatt | 2700 |
| gtttataagg aagctaagga atctgttgat gctttgtttg ttaattctca atatgatcaa | 2760 |
| ttgcaagctg atacaaatat tgctatgatt catgctgctg ataagagagt tcattctatt | 2820 |
| agagaggcat atttgcctga attgtctgtt attcctggag ttaatgctgc tatttttgaa | 2880 |
| gaattggaag gaagaatttt tactgctttt tctttgtatg atgcaagaaa tgttataaaa | 2940 |
| aatggagatt tcaataatgg attgtcttgt tggaatgtta agggacatgt tgatgttgaa | 3000 |
| gaacaaaaca atcaaagaag tgttttggtt gttcctgaat gggaagctga agtttctcaa | 3060 |
| gaagttagag tttgtcctgg aagaggatat attttgagag ttactgctta taggaagga | 3120 |
| tatggagaag gatgtgttac tattcacgaa attgaaaaca atacagatga attgaagttt | 3180 |
| tctaattgtg ttgaagaaga aatatatcct aacaatactg ttacttgtaa tgattatact | 3240 |
| gtcaatcaag aagaatatgg aggagcttat acttcaagaa atcgtggata taatgaagct | 3300 |
| ccttctgttc ctgctgatta tgcttctgtt tatgaagaaa agtcttatac tgatggaaga | 3360 |
| agagaaaatc cttgtgaatt caatagagga tatagagatt atactccttt gcctgttgga | 3420 |
| tatgttacta aggaattgga atattttcct gaaactgata aggtttggat tgaaattgga | 3480 |
| gaaactgaag gaacattcat tgttgattct gttgaattgt tgttgatgga agaatag | 3537 |

<210> SEQ ID NO 47
<211> LENGTH: 1863
<212> TYPE: DNA
<213> ORGANISM: Escherichia coli

<400> SEQUENCE: 47

| | |
|---|---|
| atggtagatc tgaggaaccg acgactcgtc cgtcctgtag aaaccccaac ccgtgaaatc | 60 |
| aaaaaactcg acggcctgtg gcattcagt ctggatcgcg aaaactgtgg aattgatcag | 120 |
| cgttggtggg aaagcgcgtt acaagaaagc cgggcaattg ctgtgccagg cagttttaac | 180 |
| gatcagttcg ccgatgcaga tattcgtaat tatgcgggca acgtctggta tcagcgcgaa | 240 |
| gtctttatac cgaaaggttg gcaggccag cgtatcgtgc tgcgtttcga tgcggtcact | 300 |
| cattacggca agtgtgggt caataatcag gaagtgatgg agcatcaggg cggctatacg | 360 |
| ccatttgaag ccgatgtcac gccgtatgtt attgccggga aaagtgtacg tatcaccgtt | 420 |
| tgtgtgaaca acgaactgaa ctggcagact atcccgccgg aatggtgat taccgacgaa | 480 |
| aacggcaaga aaaagcagtc ttacttccat gatttcttta actatgccgg aatccatcgc | 540 |
| agcgtaatgc tctacaccac gccgaacacc tgggtggacg atatcaccgt ggtgacgcat | 600 |
| gtcgcgcaag actgtaacca cgcgtctgtt gactggcagt ggtggccaa tggtgatgtc | 660 |
| agcgttgaac tgcgtgatgc ggatcaacag gtggttgcaa ctggacaagg cactagcggg | 720 |
| actttgcaag tggtgaatcc gcacctctgg caacccgggtg aaggttatct ctatgaactc | 780 |
| gaagtcacag ccaaaagcca gacagagtct gatatctacc cgcttcgcgt cggcatccgg | 840 |
| tcagtggcag tgaagggcca acagttcctg attaaccaca aaccgttcta ctttactggc | 900 |
| tttggtcgtc atgaagatgc ggacttacgt ggcaaaggat cgataacgt gctgatggtg | 960 |
| cacgaccacg cattaatgga ctggattggg gccaactcct accgtaccct gcattaccct | 1020 |

```
tacgctgaag agatgctcga ctgggcagat gaacatggca tcgtggtgat tgatgaaact   1080
gctgctgtcg gctttcagct gtctttaggc attggtttcg aagcgggcaa caagccgaaa   1140
gaactgtaca gcgaagaggc agtcaacggg gaaactcagc aagcgcactt acaggcgatt   1200
aaagagctga tagcgcgtga caaaaaccac ccaagcgtgg tgatgtggag tattgccaac   1260
gaaccggata cccgtccgca aggtgcacgg gaatatttcg cgccactggc ggaagcaacg   1320
cgtaaactcg acccgacgcg tccgatcacc tgcgtcaatg taatgttctg cgacgctcac   1380
accgatacca tcagcgatct ctttgatgtg ctgtgcctga accgttatta cggatggtat   1440
gtccaaagcg gcgatttgga aacggcagag aaggtactgg aaaagaact tctggcctgg    1500
caggagaaac tgcatcagcc gattatcatc accgaatacg gcgtggatac gttagccggg    1560
ctgcactcaa tgtacaccga catgtggagt gaagagtatc agtgtgcatg gctggatatg   1620
tatcaccgcg tctttgatcg cgtcagcgcc gtcgtcggtg aacaggtatg gaatttcgcc   1680
gattttgcga cctcgcaagg catattgcgc gttggcggta acaagaaagg gatcttcact   1740
cgcgaccgca aaccgaagtc ggcggctttt ctgctgcaaa acgctggac tggcatgaac     1800
ttcggtgaaa aaccgcagca gggaggcaaa caagctagcc accaccacca ccaccacgtg   1860
tga                                                                 1863
```

<210> SEQ ID NO 48  
<211> LENGTH: 1863  
<212> TYPE: DNA  
<213> ORGANISM: Artificial sequence  
<220> FEATURE:  
<223> OTHER INFORMATION: Synthesized

<400> SEQUENCE: 48

```
atggttgatt tgagaaatag aagattggtt agacctgttg aaactcccac aagagaaatt    60
aaaaaattgg atggattgtg ggcttttcct ttggatagag aaaattgtgg aattgatcaa   120
agatggtggg aatctgcttt gcaagaatct agagctattg ctgttcctgg atcttttaat   180
gatcaatttg ctgatgctga tattagaaat tatgctggaa atgttggta tcaaagagaa    240
gtttttattc ctaagggatg ggctggacaa agaattgttt tgagatttga tgctgttact   300
cattatggaa aagtgtgggt gaacaaccaa gaagttatgg aacatcaagg aggatatact   360
cctttttgaag ctgatgttac tcctatgtt attgctggaa agtctgttag aattactgtt   420
tgtgttaata tgaattgaa ttggcaaact attcctcctg gaatggttat tactgatgaa    480
aatgaaagag agaagcaatc ttattttcat gattttttta attatgctgg aattcataga   540
tctgttatgt tgtatactac tcctaatact tgggttgatg atattactgt tgttactcat   600
gttgctcaag attgtaatca tgcttctgtt gattggcaag ttgttgctaa tggagatgtt   660
tctgttgaat tgagagatgc tgatcaacaa gttgttgcta ctggacaagg aacttctgga   720
actttgcaag ttgttaatcc tcatttgtgg caacctggag aaggatattt gtatgaattg   780
gaagttactg ctaagtctca aactgaatct gatatttatc ctttgagagt tggaattaga   840
tctgttgctg ttaagggaca acaattttg attaatcata gccttttta ttttactgga    900
tttggaagac atgaagatgc tgatttgaga ggaaagggat tgataatgt tttgatggtg   960
catgatcatg cattaatgga ttggattgga gctaattctt atagaacttc tcattatcct  1020
tatgctgaag aaatgttgga ttgggctgat gaacatggaa tagtggtcat tgatgaaact  1080
gctgcggttg gatttcaatt gtcttttggga attggatttg aagctggaaa taagcctaag  1140
```

| | |
|---|---|
| gaattgtatt ctgaagaagc tgttaatgga gaaactcaac aagctcatct ccaagccata | 1200 |
| aaagaattga ttgctagaga taagaatcat ccttctgttg ttatgtggtc tattgctaat | 1260 |
| gaacctgata ctagacctca aggagctaga gaatattttg ctcctttggc tgaagctact | 1320 |
| agaaagttgg atcctactag acctattact tgtgttaatg ttatgttttg tgatgctcat | 1380 |
| actgatacta tttctgattt gtttgatgtt ttgtgtttga atagatatta tggatggtat | 1440 |
| gttcaatctg gagatttgga aactgctgaa aaggttttgg aaaaggaatt gttggcttgg | 1500 |
| caagaaaagt tgcatcaacc tattattatt actgaatatg gagttgatac tttggctgga | 1560 |
| ttgcattcta tgtatactga tatgtggtct gaagaatatc aatgtgcttg ttggatatg | 1620 |
| tatcatagag ttttttgatag agtttctgct gttgttggag aacaagtttg gaattttgct | 1680 |
| gattttgcta cttctcaagg aattttgaga gttggaggaa ataagaaggg aatttttact | 1740 |
| agagatagaa agcctaagtc tgctgctttt ttgttgcaaa agagatggac tggaatgaat | 1800 |
| tttggagaaa agcctcaaca aggaggaaag caagcttctc atcatcatca tcatcatgtt | 1860 |
| tag | 1863 |

<210> SEQ ID NO 49
<211> LENGTH: 3537
<212> TYPE: DNA
<213> ORGANISM: Artificial sequence
<220> FEATURE:
<223> OTHER INFORMATION: Synthesized

<400> SEQUENCE: 49

| | |
|---|---|
| atggacaaca acccgaacat caacgagtgc atcccgtaca actgcctgtc caacccggag | 60 |
| gtggaggtgc tgggcggcga gaggatcgag accggctaca cccgatcga catctccctg | 120 |
| tccctgaccc agttcctgct gtccgagttc gtgccgggcg ccggcttcgt gctgggcctg | 180 |
| gtggatataa tatggggat cttcggcccg tcccagtggg acgccttcct ggttcagatc | 240 |
| gaacaactca tcaaccaaag aatcgaggaa tttgccagaa accaagccat ctccaggctg | 300 |
| gagggcctgt ccaacctgta ccagatatac gccgagtcct caggagtg ggaggccgac | 360 |
| ccgaccaacc cggccctgag ggaggagatg aggattcagt tcaacgacat gaactccgcc | 420 |
| ctgaccaccg ccatcccgct gttcgccgtt cagaactacc aggtgccgct gctgtccgtg | 480 |
| tacgttcagg ccgccaacct gcacctgtcc gtgctgaggg acgtgtccgt gttcggccag | 540 |
| aggtggggct cgacgccgc caccatcaac tccaggtaca cgacctgac caggctgatc | 600 |
| ggcaactaca ccgactacgc cgtgaggtgg tacaacaccg gcctggagag ggtgtggggc | 660 |
| ccggactcca gggactgggt gcgatacaac caattcagga gagaattaac actcaccgtg | 720 |
| ctggacatcg tggccctgtt cccgaactac gactccagga gataccccat cagaacagtt | 780 |
| tcacaattaa caagagaaat atacaccaac ccggtgctgg agaacttcga cggctccttc | 840 |
| aggggctccg cccagggcat cgagaggtcc atcaggtccc cgcacctgat ggacatcctg | 900 |
| aactccatca ccatctacac cgacgcccac aggggctact actactggag tggacaccaa | 960 |
| ataatggcca gccggtgggc cttctccggc ccggagttca ccttcccgct gtacggcaca | 1020 |
| atggggaacg ccgccccgca gcagaggatc gtggcccaac tgggccaggg cgtatacagg | 1080 |
| accctgtcct ccaccctata caggaggccg ttcaacattg gcatcaataa tcaacaactg | 1140 |
| tccgtgctgg acggcaccga gttcgcctac ggcacctcct ccaacctgcc gtccgccgta | 1200 |
| tacaggaagt ccggcaccgt ggattcactg gatgaaattc caccgcagaa caacaacgtg | 1260 |
| ccgccgaggc agggattcag ccacaggctg tcccacgtgt ccatgttcag gtccggcttc | 1320 |

```
tccaactcct ccgtgtccat catcagggcc ccgatgtttt catggataca tcgaagcgca   1380
gaattcaata atataattgc cagcgactcc atcacccaga tcccggccgt gaagggcaac   1440
ttcctgttca acggctccgt gatctccgga cctggattca ccggcggaga cctggtgcga   1500
ttaaattcaa gcggcaacaa catccagaac aggggctaca tcgaggtgcc gatccacttc   1560
ccgtccacct ccaccaggta cagggtgagg gtgaggtacg cctccgtgac cccgatccac   1620
ctgaacgtga actggggcaa ctcctcaatt ttttcaaata cagtgccggc caccgccacc   1680
tccctggaca acctgcaatc aagcgatttc ggctacttcg agtccgccaa cgccttcacc   1740
tcctccctgg gcaacatcgt gggcgtgagg aacttctccg gcaccgccgg cgtgatcatc   1800
gacaggttcg aattcatccc ggtgaccgcc acactggagg cagaatacaa cctggagagg   1860
gcccagaagg ccgtgaacgc cctgttcaca agcacaaacc aactgggcgt gaagaccaac   1920
gtgaccgact accacatcga ccaggtgtcc aacctggtga cctacctgtc cgacgaattc   1980
tgcctggatg aaaagagaga gctgtccgag aaggtgaagc acgccaagag gctgtccgac   2040
gagaggaacc tgttgcagga ctccaatttc aaagacatta atcgacagcc ggagagggc    2100 tggggcggct ccaccggcat caccatccag ggcggcgacg acgttttcaa ggagaactac   2160
gtgaccctgt ccggcacctt cgacgagtgc tacccgacct acctgtacca agatcgat    2220 gaatcaaaat taaaggcatt cacaagatac caattaagag gatacatcga ggactcccag   2280
gacctggaga tatacctgat caggtacaat gcaaaacatg aaacagtcaa cgtgccgggc   2340
accggctccc tgtggccgct gtccgcccag tccccgatcg gcaagtgcgg cgagccgaac   2400
aggtgcgccc cgcacctgga gtggaacccg gacctggact gctcatgcag ggacggcgag   2460
aagtgcgccc accactccca ccacttctcc ctggacatcg acgtgggctg caccgacctg   2520
aacgaggacc tgggcgtgtg ggtgatcttc aagatcaaga cccaggacgg ccacgccagg   2580
ctgggcaacc tggagttcct ggaggagaag ccgctggtgg cgaggccct ggccagggtg    2640 aagagggccg agaagaagtg gagggacaag agggagaagc tggagtggga gaccaacatc   2700
gtatacaagg aggccaagga gtccgtggac gccctgttcg tgaactccca gtacgaccaa   2760
ttgcaggccg acaccaacat cgccatgatc cacgccgccg acaagagggt gcactccatc   2820
agggaggcct acctgccgga gctgtccgtg attcctggcg tgaacgccgc catcttcgag   2880
gagctggagg caggatcctt caccgccttc tccctgtacg acgccagaaa tgtcataaaa   2940
aatggcgatt tcaataatgg actgtcctgc tggaacgtga agggccacgt ggacgtggaa   3000
gaacagaaca ccaaagaag cgtgctggtg gtgccggagt gggaggccga ggtgtcccag   3060
gaggtgaggg tgtgccctgg caggggctac atcctgaggg tgaccgccta caaggagggc   3120
tacggcgagg gctgcgtgac catccacgag atcgagaaca atacagatga gctgaagttc   3180
tccaactgcg tggaggagga gatatacccg aacaacaccg tgacctgcaa cgactacaca   3240
gtcaaccaag aagagtacgg cggcgcctac acctcaagaa accgtggata taatgaggcc   3300
ccgtccgtgc cggccgacta cgcctccgtg tacgaggaga gtcctacac cgacggcagg   3360 agggagaacc cgtgcgaatt caacagggc tacagggact acacccgct gccggtgggc    3420 tacgtgacca aggagctgga gtacttcccg agaccgaca aggtgtggat cgagatcggc    3480
gagaccgagg gcacattcat cgtggactcc gtggagctgc tgctgatgga ggagtag      3537
```